United States Patent
Salcudean et al.

(10) Patent No.: US 7,662,128 B2
(45) Date of Patent: Feb. 16, 2010

(54) STEERABLE NEEDLE

(76) Inventors: Septimiu E. Salcudean, 3936 West 32nd Avenue, Vancouver, B.C. (CA) V6S 1Z3; Robert N. Rohling, 133 West 20th Avenue, Vancouver, B.C. (CA) V5Y 2C4; Stephen H. Okazawa, 1848 Collingwood Street, Vancouver, B.C. (CA) V6R 3K5; Afrooz R. Ebrahimi, Appt 2804, 7 Concorde Place, North York, ON (CA) M3C 3N4

( * ) Notice: Subject to any disclaimer, the term of this patent is extended or adjusted under 35 U.S.C. 154(b) by 1096 days.

(21) Appl. No.: 10/737,958

(22) Filed: Dec. 18, 2003

(65) Prior Publication Data
US 2004/0133168 A1 Jul. 8, 2004

(51) Int. Cl.
- A61M 31/00 (2006.01)
- A61N 1/30 (2006.01)
- A61M 5/00 (2006.01)
- A61M 25/00 (2006.01)

(52) U.S. Cl. ............... 604/93.01; 604/19; 604/117; 604/530

(58) Field of Classification Search ............... 600/567, 600/566, 564, 558, 562; 604/264, 187, 239, 604/240, 263, 44, 158, 161, 164.11, 60; 606/144, 606/167, 185; 607/101, 103, 99
See application file for complete search history.

(56) References Cited

U.S. PATENT DOCUMENTS

| 3,069,654 | A | * | 12/1962 | Hough | 382/281 |
| 3,773,034 | A | * | 11/1973 | Burns et al. | 600/434 |
| 4,874,376 | A | * | 10/1989 | Hawkins, Jr. | 604/165.01 |
| 5,345,937 | A | | 9/1994 | Middleman et al. | |
| 5,807,324 | A | * | 9/1998 | Griffin, III | 604/529 |
| 6,146,380 | A | | 11/2000 | Racz et al. | |
| 6,165,139 | A | * | 12/2000 | Damadian | 600/585 |
| 6,190,353 | B1 | | 2/2001 | Kakower et al. | |
| 6,217,554 | B1 | | 4/2001 | Green | |
| 6,228,049 | B1 | | 5/2001 | Schroeder et al. | |
| 6,425,887 | B1 | | 7/2002 | McGuckin et al. | |
| 6,602,185 | B1 | * | 8/2003 | Uchikubo | 600/118 |
| 7,169,155 | B2 | * | 1/2007 | Chu et al. | 606/130 |

* cited by examiner

*Primary Examiner*—Nicholas D Lucchesi
*Assistant Examiner*—Ian K Holloway
(74) *Attorney, Agent, or Firm*—C. A. Rowley

(57) ABSTRACT

The invention relates to a needle guidance system provided by a needle with a steerable tip. The needle has a cannula and a stylet. The stylet adjacent to its tip has a naturally curved portion. The stylet is movable in two degrees of freedom with respect to the cannula—axial translation and axial rotation with respect to the cannula axis. When extended, the stylet curves off-axis and provides cannula tip steering. Driving and/or steering systems may be provided to the orientation and relatively move the stylet.

22 Claims, 13 Drawing Sheets

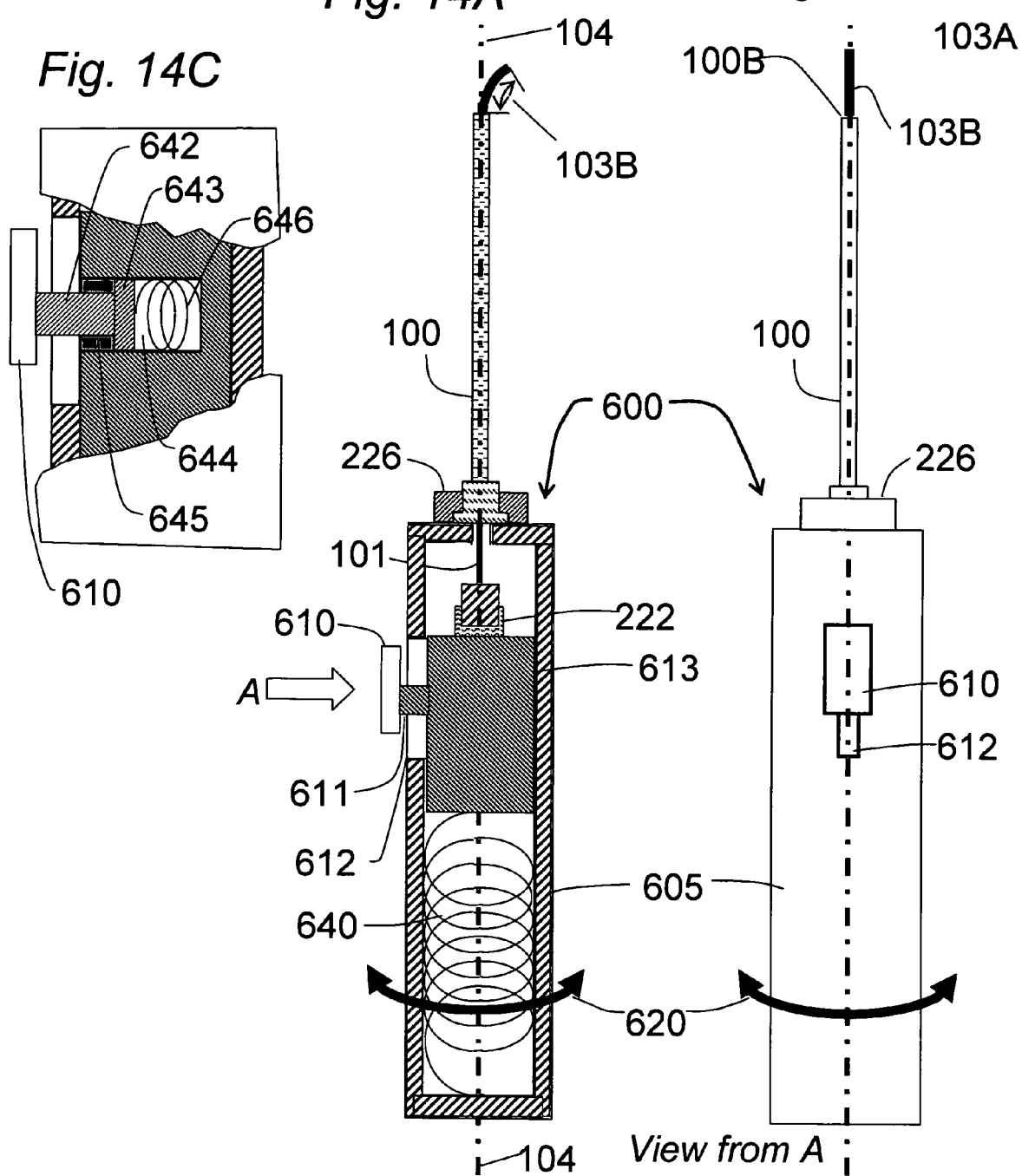

STEERABLE NEEDLE

FIELD OF THE INVENTION

The invention relates to an improved needle that may be guided to a target.

BACKGROUND TO THE PRESENT INVENTION

Minimally invasive, percutaneous procedures have a wide variety of applications in medical diagnosis and therapy. Biopsy, delivery of localized therapy, and anesthesia are performed quickly and with minimal patient trauma using long, fine needles to access the desired site within the body via a puncture from the skin surface.

A significant factor limiting the success of minimally invasive, percutaneous procedures is the limited degree of control available to the operator over the path of the needle. Once the needle tip has pierced the skin along the chosen axial trajectory, the operator has direct control only over insertion depth. Choosing the correct insertion angle is itself challenging but compounding this difficulty is the tendency of fine needles (typically 20-22 gauge) to wander laterally from the insertion axis as the needle advances through the patient's tissue. This lateral wandering effect is caused by several factors including the bevel cut faces of the needle, inhomogeneous tissue properties such as friction and elasticity, and unintentional lateral forces applied to the needle base by the operator's hand. We have observed in the laboratory that these effects can noticeably bend the needle away from its apparent axis at the base resulting in a missed target and the need to perform a second insertion. This effect has also been observed in clinical practice, even under real-time image guidance. For example, see the article "US-guided nephrostomy with the aid of a magnetic field-based navigation device in the porcine pelvical-iceal system", Krombach G A, Mahnken A, Tacke J, Staatz G, Haller S, Nolte-Ernsting C C A, Meyer J, Haage P, Gunther R W, Journal of Vascular and Interventional Radiology, 12 (5), pp. 623-628, May 2001.

Many biopsies, however, require fluid or cell samples for diagnosis by a pathologist. For these cytological biopsies, fine needles are normally used. Other procedures such as amniocentesis involve direct suction from fluid cavities in the body and similarly require the use of fine needles often at depths exceeding 10 cm.

An additional limitation to the success of percutaneous needle procedures is the presence of bones, major blood vessels, nerves and other sensitive features in the body that may not leave a straight-line access to the target. In such instances, minimally invasive needle procedures are generally not possible and the physician may then have to resort to surgery.

The desire to access targets that reside laterally from the available insertion trajectory is evident in many recent US patents. McGuckin et al., in U.S. Pat. No. 6,425,887, describe a system consisting of a large outer cannula containing many smaller needles inside. Advancing the inner needles causes them to exit the outer cannula laterally in all directions. Schroeder et al., in U.S. Pat. No. 6,228,049, describe a needle introducer with a laterally inclined exit hole such that a flexible needle may be inserted through the introducer to access lateral target sites. Racz et al., in U.S. Pat. No. 6,146,380, describe a surgical probe with a rigid, bent tip to allow steering freedom inside the body. Finally, several patents describe catheters that allow a lateral degree of freedom at the tip. U.S. Pat. Nos. 6,217,554 and 6,190,353 describe catheters in which a needle inserted through the catheter exits the tip with a strong lateral curve, and in U.S. Pat. No. 5,345,937, Middleman et al. describe a system allowing the tip of the catheter cannula to be bent in any desired direction to aid in navigating the blood vessels.

None of these patents provides the equipment or methodology to variably steer a medical needle during its insertion. U.S. Pat. Nos. 6,425,887, 6,228,049, 6,217,554, and 6,190,353 cited above only provide methods of lateral access to target sites from traditional access routes, by a straight-line needle insertion or catheter blood-vessel navigation. This prior art does not describe how to steer a needle during insertion to generate a prescribed path.

U.S. Pat. No. 6,146,380 describes steering a surgical probe with a bent tip, but the curvature of the tip is fixed which allows the physician to control steering direction but not magnitude, and the probe does not track straight.

U.S. Pat. No. 5,345,937 describes a catheter steering system suitable for aiding in navigating branching blood vessels with a flexible catheter tube, but this system cannot steer fine, stiff needles through the body's flesh.

None of the existing systems provides motorized or computer-controlled actuation of the needle components nor do they provide visual feedback to aid in the physician's understanding and visualization of the needle and target positions inside the body.

Larger needles (18 gauge or less) are usually stiff enough that they do not wander off the axis during insertion, but these needles are generally used in core biopsies when solid tissue samples are required.

BRIEF DESCRIPTION OF THE PRESENT INVENTION

The invention relates to a needle guidance system comprised of a needle with a steerable tip, an actuation system, a medical imaging device, a position sensor, and computing systems that detect the needle in a medical image, determine the location of the needle in space, calculate current and desired paths for needle motion, and provide guidance to the operator via visual aids.

It is the object of the present invention to provide the operator with an interface device and a steering control unit to steer the needle.

It is another object of this invention to provide a position sensor to freehand ultrasound needle guidance and provide an improved level of guidance to the operator.

Broadly the present invention relates to a needle structure comprising a hollow, outer cannula having a main longitudinal axis and an open end, and a longer stylet having a leading end adjacent to said open end and having a curved portion with a pre-defined curvature adjacent to said leading end, mounting means mounting said stylet coaxially within said outer cannula so that said stylet and cannula may be relatively translated along said main axis from a sheathed position wherein substantially all of said curved portion of said stylet is within said cannula to an extended position wherein a selected extended part of said curved portion of said stylet projects beyond said open end, said cannula being stiffer than said stylet, so that when said stylet is in its said sheathed position it assumes a shape defined by said cannula, and when said stylet is in its said extended position, said extended part of said stylet assumes a curved shape primarily determined by said pre-defined curvature, and said leading end extends from said cannula in a direction determined by the rotation of said stylet about said main axis.

Preferably said mounting means mounts said stylet to also permit relative rotational movement of said stylet and said cannula.

Preferably said needle structure further comprises means for indicating said direction of said leading end.

Preferably said means for indicating comprises marking on said stylet.

Preferably said needle structure further comprises a casing, drive means, said drive means including means to rotate said stylet about said main axis and means to relatively move said stylet and said cannula along said main axis from said sheathed position to said extended position, said means to rotate and said means to translate being mounted within said casing.

Preferably said means to relatively move moves said stylet relative to said cannula and said means to rotate and said means to relatively move are connected to said stylet and said cannula is fixed to said casing.

Preferably said needle structure further comprises sensing means for sensing the rotation of said stylet relative to said casing and further means for sensing said extended position of said stylet, operator input means for specifying a desired said direction and a desired said extended position, and computer means for controlling said means to rotate and said means to relatively move to achieve said desired direction and desired extended position.

Preferably said operator input means are mounted on said casing.

Preferably said operator input means includes a stylet rotation control and a movement control means for controlling said means to relatively move, said rotation control determining said direction relative to said casing, and said movement control means determining said extended part.

Preferably said needle structure further comprises a medical imaging system to sense the position of a target to which said needle structure is directed, computer means to provide a detected position of said cannula within the images provided by said medical imaging system, and display means for displaying said target and said detected position of said cannula to an operator.

Preferably said needle structure further comprises sensing means for sensing the position of said needle structure, computer means for expressing said sensed position of said needle structure in the coordinates of said medical imaging system, and means for superimposing said sensed position of said needle structure in said coordinates of said medical imaging system onto said display means to display said sensed position of said needle structure with said target and said detected position of said cannula in a manner to assist an operator in steering said needle structure.

Preferably said needle structure further comprises a mechanical guide, said mechanical guide facilitating alignment of said cannula to the said display means.

Preferably said computer means generates a path to said target and displays it on said display means Preferably said needle structure further comprises means for applying a small motion pattern to said stylet, said small motion pattern being detectable by medical imaging techniques.

Preferably said computer means includes means for calculating a path for said cannula.

Preferably computer generates a sequence of said desired directions and set desired extended positions of said stylet to effect a cannula path to said target as the operator moves said needle structure.

Preferably said needle structure further comprises a robot and wherein said computer includes means for controlling said robot to insert said needle structure on said path.

Preferably said cannula has a reinforced segment of higher stiffness adjacent to said open end.

Broadly the present invention also relates to a method of controlling the path of movement of a needle structure toward a target wherein said needle structure comprises a hollow outer cannula having a main longitudinal axis and an open end, a stylet having a curved portion having a defined curvature adjacent to its leading end, said stylet being mounted coaxially within said outer cannula with said leading end adjacent to said open end, so that said stylet may be rotated about said main axis and said stylet and cannula relatively moved axially relative to said main axis between a sheathed position wherein said curved portion of said stylet is within said cannula to an extended position wherein said stylet projects a selected distance beyond said free end to provide a curved extended part of said stylet having a curvature approaching said defined curvature with said leading end extending from said cannula in a controlled direction determined by rotation of said stylet about said main axis, said method comprising, moving said stylet and said cannula on said path in a selected direction toward said target and adjusting said selected direction by rotating said stylet within said cannula to a selected orientation and then relatively moving said stylet and said cannula to position said stylet in said extended position, and to provide said curved extended part with said leading end pointing in said controlled direction determined by said selected rotation, then advancing the needle along said path in an adjusted direction.

Preferably said relatively moving comprises moving said stylet relative to said cannula. The present invention also relates to a method of detecting a needle in an ultrasound image comprising median filtering to remove speckle noise, detecting needle point candidates at the peaks in the derivative function along several directions perpendicular to an approximate direction of the needle, fitting such point candidates to a line, using a Hough transform improve on the resulting line, and finding a polynomial fit to those needle point candidates that are close to the line determined by the Hough transform.

BRIEF DESCRIPTION OF THE DRAWINGS

Further features, objects and advantages of the present invention will be evident from the detailed description of the present invention taken in conjunction with the accompanying drawings in which;

FIG. 14A is a section through a simplified design of needle structure of the present invention.

FIG. 14B is a plan view of the simplified design shown in FIG. 14A but with the structure rotated 90 on its longitudinal axis.

FIG. 14C is a partial section showing a locking system for holding and releasing the slider for axial movement.

DETAILED DESCRIPTION OF THE PREFERRED EMBODIMENTS OF PRESENT INVENTION

Basic Needle Structure

Figures 1, 2:
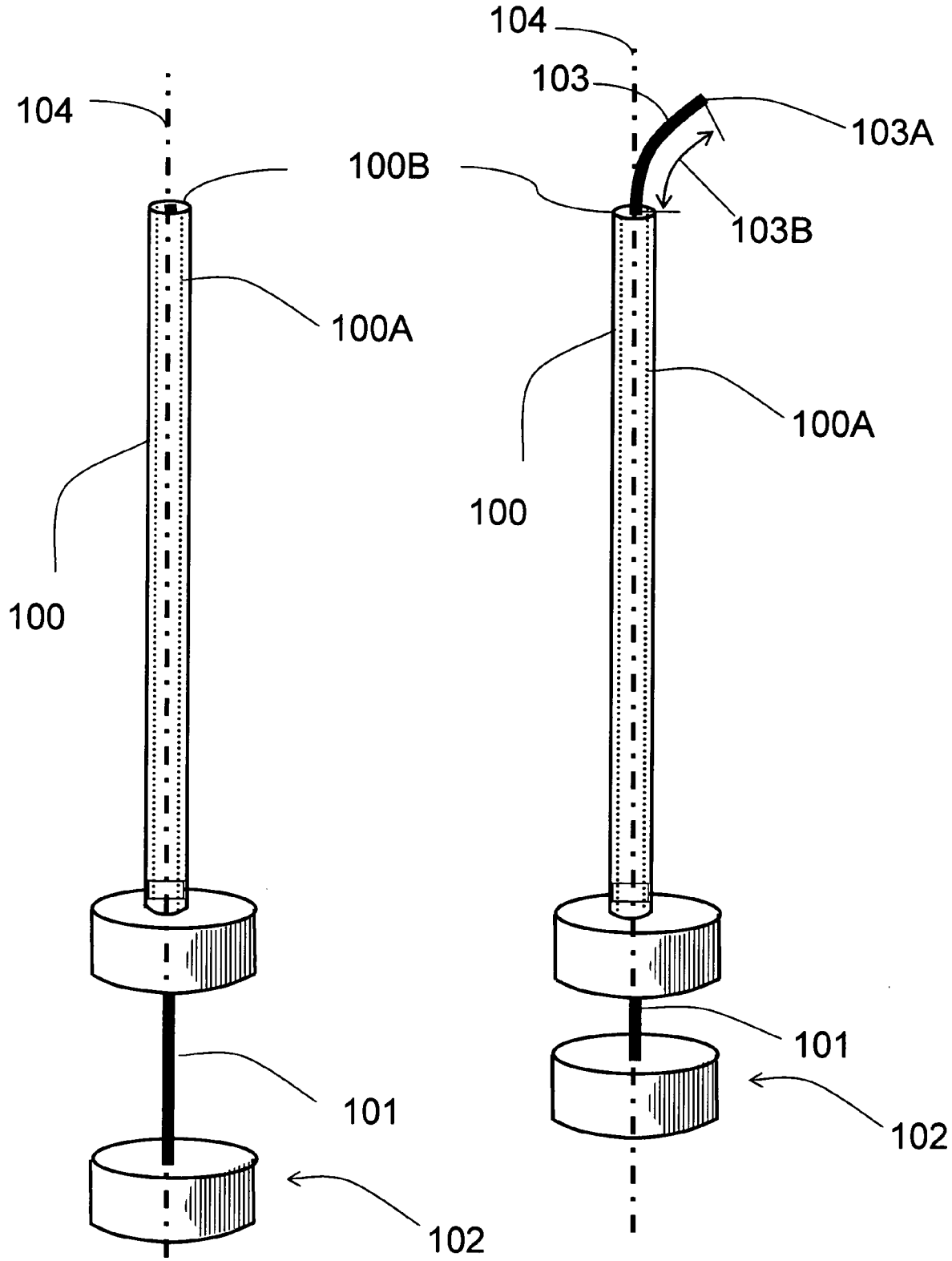
FIG. 1 shows the medical needle in its straight-tip configuration.
FIG. 2 shows the medical needle in its bent-tip configuration.

As shown in FIGS. 1 and 2, the needle 102 consists of two parts, namely, a cannula 100 having a hollow core 100A and a stylet 101 received within the hollow core 100A. The tubular or hollow cannula 100 in its natural unconstrained state is straight i.e. has a straight main or longitudinal axis 104. The stylet 101 is preferably a solid cylindrical element that may be inserted into the hollow core 100A of the cannula 100. The stylet 101 has a curved portion 103 adjacent to its free or leading end 103A that has a defined curvature in its natural unconstrained state. This curvature is preferably a smooth curve to allow the stylet to be easily extended into tissue and minimize tissue damage.

Typically, this curved end portion 103 of the stylet 101 extends from the free end or tip 103A up to about 2 centimeters (cm) and normally will have a curvature having a radius as small as 0.2 cm. Obviously the specific curvature and length of the curved portion 103 will be selected for the specific application to which the needle is to be applied.

In its normal unconstrained state, the cannula 100 is stiffer than the stylet 101. Therefore, when the curved portion 103 of the stylet is retracted within the cannula hollow core 100A (sheathed position); the stylet curved portion 103 is constrained to be in a substantially straight condition by the cannula 100. As shown in FIG. 2, when the stylet tip 103A is pushed out past the cannula tip 100B of the cannula 100 (i.e. the stylet and cannula are relatively translated), the exposed part or extended part 103B of the curved portion 103 of the stylet 101 will emerge in its naturally curved state. The length of the exposed part 103B is controlled by the user of the device.

Although not shown in FIGS. 1 and 2, the cannula may be and is likely to be beveled. As well, the stylet could also be beveled or sharpened.

In experiments performed by the inventors on tissue mimicking phantoms, it was found that a cannula bevel does indeed tend to steer the needle a small amount. This steering effect can be cancelled almost precisely by extending the stylet a small amount in such a way that the stylet is curved opposite the bevel angle. The cannula bevel and stylet exposed curved portion 103B in effect cancelled each other's steering effects.

Figure 3:
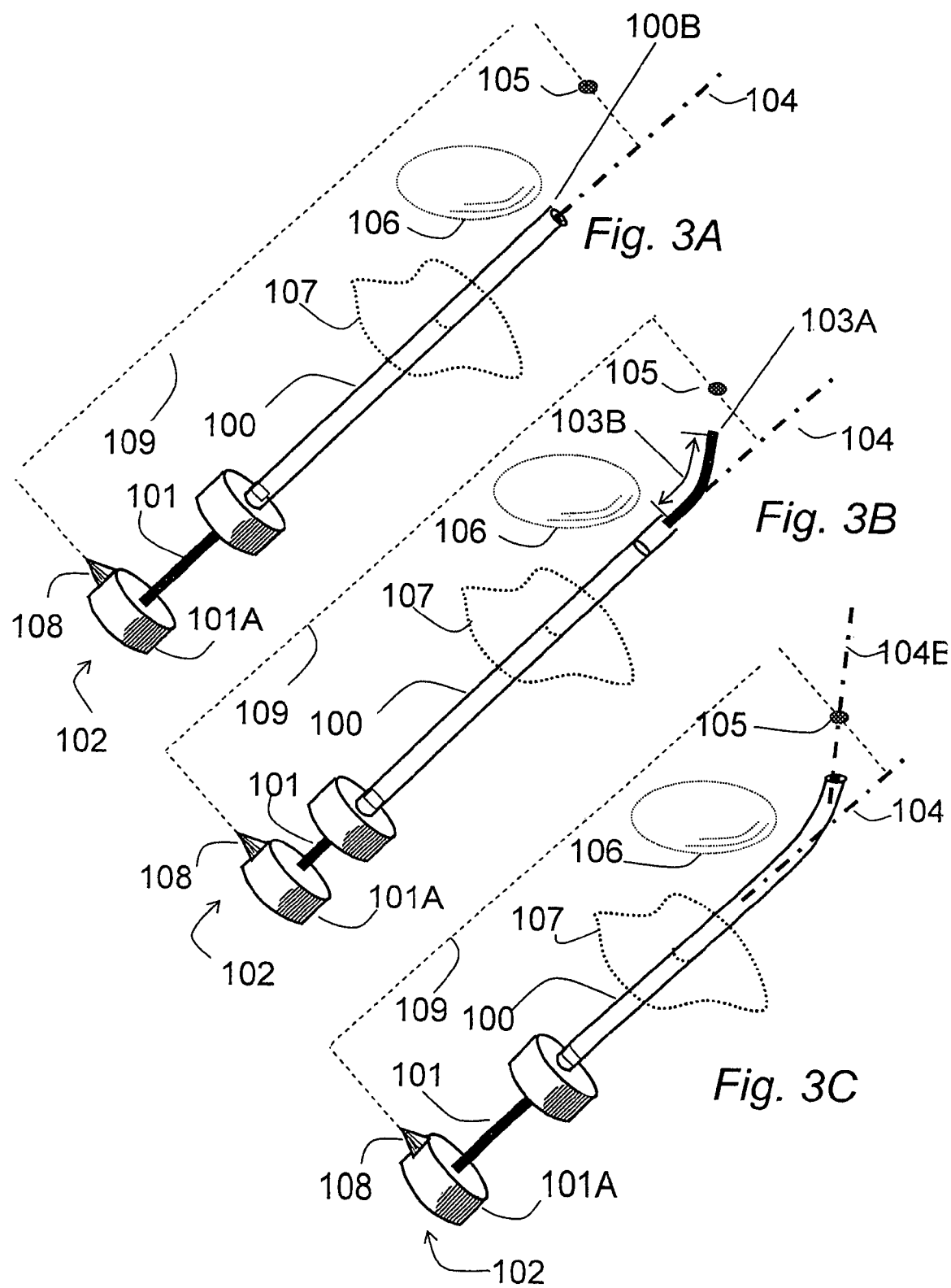
FIG. 3A depicts the first step of a needle insertion procedure with the stylet initially retracted within the cannula, providing a straight tip.
FIG. 3B depicts the second step of a needle insertion procedure where the stylet has been extended from the cannula, providing a bent tip.
FIG. 3C depicts the third step of a needle insertion procedure where the cannula has followed the curve of the stylet, and thus demonstrating needle steering.

In use the cannula 100 of needle 102 of the present invention is steered by rotating the stylet to the desired orientation about the longitudinal axis 104 of the cannula 100 and advancing the stylet 101 along the longitudinal axis 104 of the cannula 100 to expose at least a part 103B of the curved portion 103 of the stylet 101. (It will be apparent that it is also possible to first advance the stylet and then orient it but this is likely to be more painful and thus normally will not be used.) Once a fraction (extended part) 103B of the curved portion 103 of the stylet 101 is exposed, pushing the cannula 100 and stylet 101 together into the tissue while keeping the exposed part of the stylet 103B in extended position e.g. at a constant length will deflect the cannula and stylet and/or displace the deformable surrounding tissue so that the stylet tip 103A moves in the direction of the exposed or extended curved portion 103B of the stylet 101 i.e. the open end 100B of the cannula id deflected toward the tip 103A as indicated schematically by the shift in axis direction as shown at 104B in FIG. 3C. Retracting the stylet 101 into the cannula (or advancing the cannula with respect to the stylet if such action is provided for in the structure) will retract the extended portion 103B of the curved part 103 of the stylet, allowing the needle to continue being inserted in an essential straight manner but with the leading end 100B of the cannula moving in an adjusted direction determined by amount or length of the exposed or extended portion 103B. The operation of the invention is illustrated in FIGS. 3A, 3B, 3C, that show a needle 102 being inserted and the free end 103A of the stylet steered towards a target 105 past an obstacle schematically indicated at 106. FIG. 3A shows the needle 102 having penetrated the skin surface schematically indicated 107. An obstacle 106 prevents direct access to the target 105. Indeed, penetration of the needle 102 in the direction shown in FIG. 3A will entirely miss the target 105 and obstacle 106. As shown in FIG. 3A, the needle 102 is inserted in an approximately straight line i.e. in the direction of the longitudinal axis 104 to a position wherein the obstacle 106 may be avoided, the stylet 101 is then be pushed out beyond the free end 100B of the cannula 100, into an extended position to provide an extended part 103B as shown in FIG. 3B. The extended part 103B of the curved portion 103 of stylet 101 will assume or approach its naturally bent or curved state as it is moved out of the cannula 100.

Next the stylet 101 and the cannula 100 are moved together into the tissue and the extended portion 103B deflect the advancement of the needle 102. It will be apparent that to a degree the amount the needle 102 is deflected is based on the curvature and length of the extended portion 103B and the nature of the tissue being penetrated. When the desired deflection of the needle 102 has been achieved the stylet 101 may be retracted back into the cannula 100 and advancement of the needle 102 continued as desired.

It is believed the operation is as follows. As is apparent the stylet is a cylindrical structure tapering to a cone, or a bevel. The tissue in front of the cannula, as the stylet and cannula get pushed forward, is deformed (compressed) and therefore pushes back on the needle with a (restoring) force that has a component tangential to the needle cannula (the direction in which the cannula is shoved into the tissue), and a direction that is *normal* to the needle cannula. The nature of the force and the exact trajectory that results is an extremely complicated function of stylet stiffness, tissue stiffness, cannula stiffness, as well as of the stylet plus cannula friction with tissue. Clearly in very aqueous gelatin there would be very little deflection unless the needle moves very fast. However, in a tissue structure that might have an almost rigid cloth like structure, where the stylet opens up a slight curved channel, the normal forces would be so large as to make the cannula follow the stylet curve exactly. In general the cannula will not follow the stylet curvature but it will follow a reduced curvature because it is stiffer.

It has been found that if the tissue structure is significantly softer than the cannula 100, the cannula 100 may not be deflected and may simply deform the tissue to a new shape that pushes the obstacle out of the way and pulls the target into the path of the needle.

Should it be necessary to again change the course or direction of the needle path the process is repeated by orienting the stylet 101, extending the curved portion and advancing the needle 102 as above described to again adjust the direction of penetration of the needle 102.

Obviously the stylet 101 must be oriented spatially towards the target 105 to ensure the projecting portion 103B projects at the correct orientation from the cannula 100. To do this it is necessary to know its orientation relative to the tissue. In the embodiment illustrated in FIGS. 3A, 3B and 3C a marker 108 on the base of the stylet 101 provides this knowledge. This marker 108 may take the form of a flat area, an arrow, a color marker, etc. and indicates the direction of an axial plane 109 oriented radially relative to the axis 104 and containing the bent stylet section 103. Thus the orientation of this marker 108 indicates the orientation of the stylet extended portion section 103B relative to the tissue and can be employed by the operator, as described above, to navigate the needle 102 towards a target 105 or away from an obstacle 106.

The construction of a manual steerable needle as described above required three changes to a conventional needle: (i) the stylet 101 is longer than the cannula 100, (ii) the stylet is curved as indicated at 103 (this can be accomplished by standard techniques, such as compression of the needle tip between two mating parts, one having a half-cylinder hollowed out, the other being cylindrical with radius smaller than the hollowed-out cylinder by the stylet diameter), and (iii) the stylet base 101A should have a rotation indicator 108 as described above and showed in FIGS. 3A, 3B, 3C.

Figure 13:
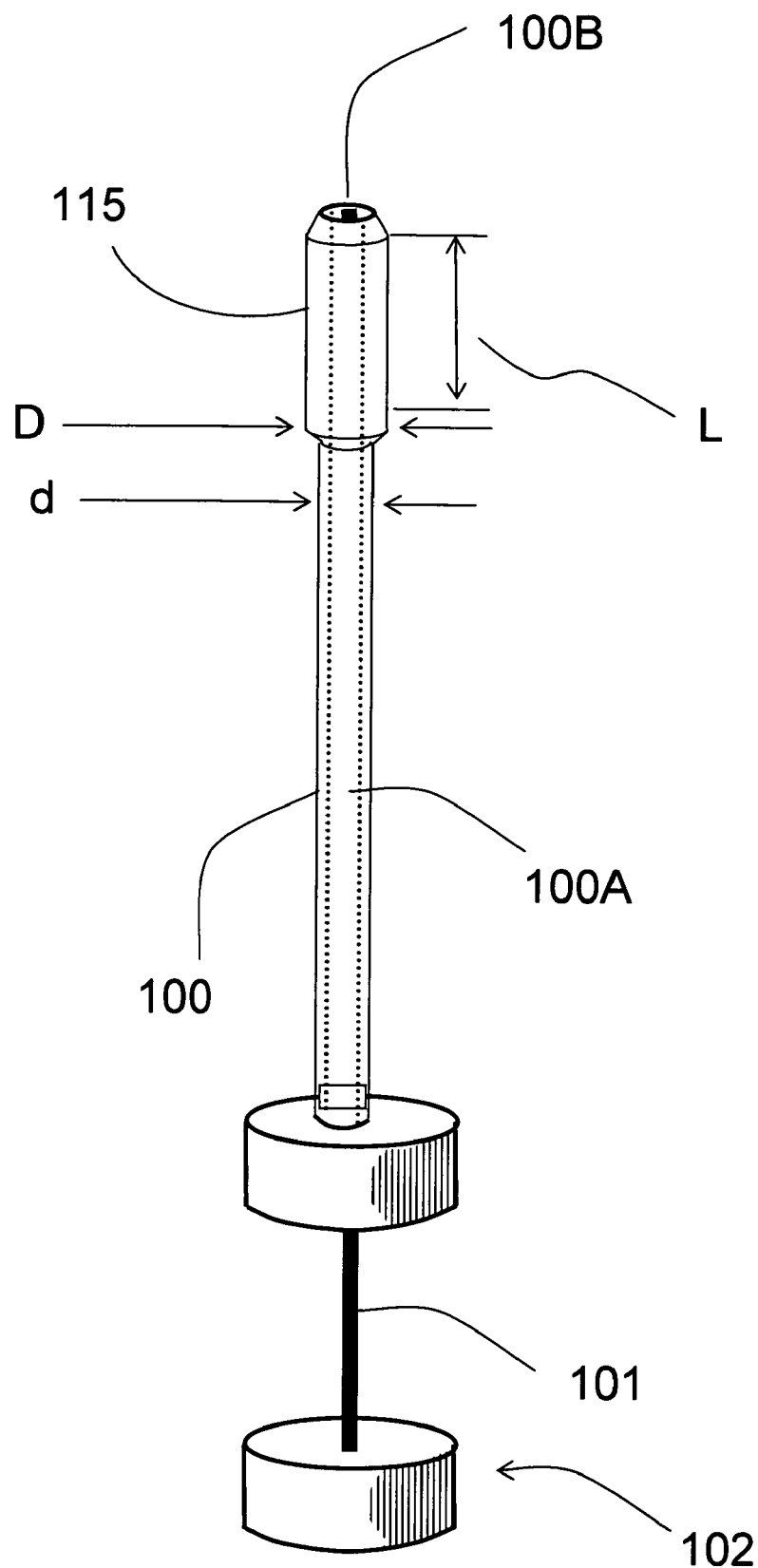
FIG. 13 is a view similar to FIG. 1 but showing a modified cannula structure.

It is possible to manufacture the cannula so that it is stiffer near its tip. More precisely, as shown in FIGS. 2 and 13, if the curved part of the stylet 103 spans a length L, the cannula could have a reinforced section 115 starting at its tip 100B and extending at least an equal length L away from the tip 100B towards the proximal end of the cannula 100. The reinforced section 115 could be stiffer simply due its larger diameter D, as opposed to the smaller diameter d used for the rest of the cannula. Alternatively, the reinforced section could be made stiffer by the use of a different material and/or by thermal treatment.

A cannula that is stiffer near the tip has the advantage that when the curved portion 103 of the stylet 101 is fully retracted within the hollow core 100A of the cannula, there will be less deformation of the cannula tip and therefore, when the stylet 101 is not extended out of the cannula 100, the cannula travel will be closer to a straight line. At the same time, not all the length of the cannula needs to be made stiffer in order to achieve this, in effect allowing trajectories that will be reasonably "tortuous", while at the same time being able to execute straighter trajectories. It will be apparent that any curving or bending of the cannula will not like occur in reinforce section 115 but will commence on the side of the reinforcing 115 remote from the open end 100B It is clear from the above description and from FIGS. 3A, 3B, 3C, that the navigation of the steerable needle 102 with the curved stylet 101, straight cannula 100, and stylet orientation marker 108, is a difficult task requiring that the operator have excellent spatial imaging ability and hand coordination ability within this spatial image. Furthermore, two hands are needed to orient and translate the stylet 101 and the cannula 100 independently from each other.

This implies that an additional imaging device that depicts the needle insertion if used must be operated by an assistant. In addition to the steerable needle 102 described above, this invention provides solutions to the needle navigation problem in the form of an actuated steerable needle and a needle navigation system as described below.

FIGS. 14A and 14B show a simplified form of needle structure 600 that may be produce at a very low cost permitting it to be used and disposed of economically. The needle structure 600 consists of a casing 605 to which the cannula 100 is attached via a locking mechanism 226. A stylet connector 222 is attached to the stylet 101 to a linear slider 613 that can translate but is prevented from rotation by any suitable means (such as the element 611 and the side edges of the slot 612) inside the casing 605. A connecting element 611 (shown in FIG. 14A) extends through a slot 612 in the casing 605 and connects the slider 613 internal to the casing 605 to a manipulating element or button 610 external to the casing 605.

Translation of the slider 613 along the stylet and cannula axis 104 is achieved through the translation of the element 610.

FIG. 14A is a cross section showing the slider in the mid-position of its sliding range as determined by the axial length of the slot 612 which in the illustrated arrangement corresponds to the extended portion 103B of the stylet 101 extended about half its maximum extension.

FIG. 14B is a plan view with the needle 600 rotated 90 degrees relative to the orientation shown in FIG. 14A about the axis 104 and with the stylet 101 extended further from the open end 100B of cannula 100.

A change in direction of the stylet tip is achieved by a rotation of the entire needle structure 600 i.e. casing 605 cannula 100 and stylet 101 about the axis 104 as schematically indicated by arrow 620.

This needle structure 600 has the advantage that can be operated fully manually. Its disadvantage is that in order to re-orient the direction of the stylet extended portion 103B, the cannula 100 must be rotated together with the stylet 101.

In operation, the user holds the casing 605 as a handle orients the curved portion 103 by rotating the whole needle structure 600 about the axis 104 as schematically indicated by arrow 620 to the desired orientation as described above and pushes the button 610 to the position as needed with his/her thumb to move the stylet axially to provided a selected appropriate stylet extended portion 103B. It is a simple matter to adjust the length of the extended part 103B by sliding the button 610 back and forth. The needle structure 600 is then moved substantially axially in a direction substantially parallel to the axis 104 and the extended portion 103B steers the open end 100B of the cannula 100 in the selected direction. A number of features that may improve the ergonomic handling of a needle structure 600 shown in FIGS. 14A and 14B can be added. For example a spring schematically shown at 640 that pulls the slider 613 to retracted position wherein the stylet 101 is in sheathed position within the cannula 100 so that when the user releases the button 610, the stylet retracts fully.

A locking mechanism for the stylet in an extended position e.g., for a selected degree of extension can also be employed. As shown in FIG. 14C the element 611 may be formed as a shaft portion 642 interconnecting the button element 610 with a retainer flange portion 643 that is trapped in a suitable passage 644 formed in the slider 613 and biased to press against a friction ring 645 slidable in the passage 644 and pressed against the casing 605 on opposite sides of the slot 612 by the spring 646 acting through the flange 643. Applying pressure in the direction A on the button 610 in FIG. 14A moves the flange 643 which releases the pressure on friction ring 645 which disengages with casing 605 so that the stylet 101 is easily moved axially when the button 610 is depressed. When the button 610 is released, the stylet 101 becomes difficult to move.

Obviously the casing 605 will be constructed to permit easy access to the stylet through a screw-on or bayonet cap.

If desired and for purposes described below an oscillatory or other small motion of the stylet to make the imaging of the stylet tip 103B easier can be added by mounting a small linear actuator (not indicated) between the slider 613 and the stylet connector 222.

Also if desired the manual stylet extension mechanism button 610 described with reference to FIGS. 14A and 14B can be replaced with an operator-controlled single linear motor 210, as described below.

Hand-Held Actuated Steerable Needle

As discussed above, the motions required to steer the needle 102 are rotation and extension of the stylet 101 with respect to the cannula 100 and then advancement of the needle 102. The two motions by the stylet 101 can be actuated by a needle actuator structure 200, one embodiment of which is shown schematically in FIG. 4.

A rotary actuator 210 is mounted to an enclosure 205 and rotates the mounting shaft 212 about the common axis 104 of the stylet 101 and cannula 100. A linear actuator 215 is fixed to the mounting shaft 212. An additional rotary bearing 206 may be used as a support for the linear actuator 215 in the enclosure or housing 205. The linear actuator 215 can translate as indicated by the arrow 216 the shaft 220 of the actuator 215 along the common axis 104 of the stylet 101 and cannula 100 while preventing relative rotation therebetween. The stylet 101 is attached to the shaft 220 using a locking mechanism 222 and the cannula 100 is attached to the enclosure 205 using a second locking mechanism 226.

By controlling how far the linear actuator shaft 220 moves with respect to the actuator 215 (and thus relative to the housing 205 and cannula 100, the axial extension of the stylet 101 from within the cannula 100 can be controlled. By controlling how much the shaft 212 is rotated by the actuator 210, the rotation angle of the actuator 215 and thus the stylet 101 about axis 104 with respect to the cannula 100 can be controlled. The rotation angle of the stylet 101 with respect to the enclosure 205 determines the direction of the axial plane containing the curved portion 103A of the stylet 101 in which direction the stylet 101 will be when exiting the cannula 100.

The rotary actuator 210 and the linear actuator 215 both require external electrical circuits for supply of power, and actuation signals. The rotary actuator's power supply and the linear actuator's power supply are schematically indicated at 250 and 253 respectively are shown as inputs. Alternatively, the actuators can be supplied by power from batteries mounted internal to the needle actuator structure 200.

The rotary actuator's actuation signal and the linear actuator's actuation signal are schematically indicated at 251 and 254 respectively as inputs to the system. Typically the actuators 210 and 215 each contain a built-in sensor to measure the true displacement. The signals representing the rotary actuator's angular displacement and the linear actuator's linear displacement are schematically indicated at 252 and 255 are shown as outputs.

Figure 4:
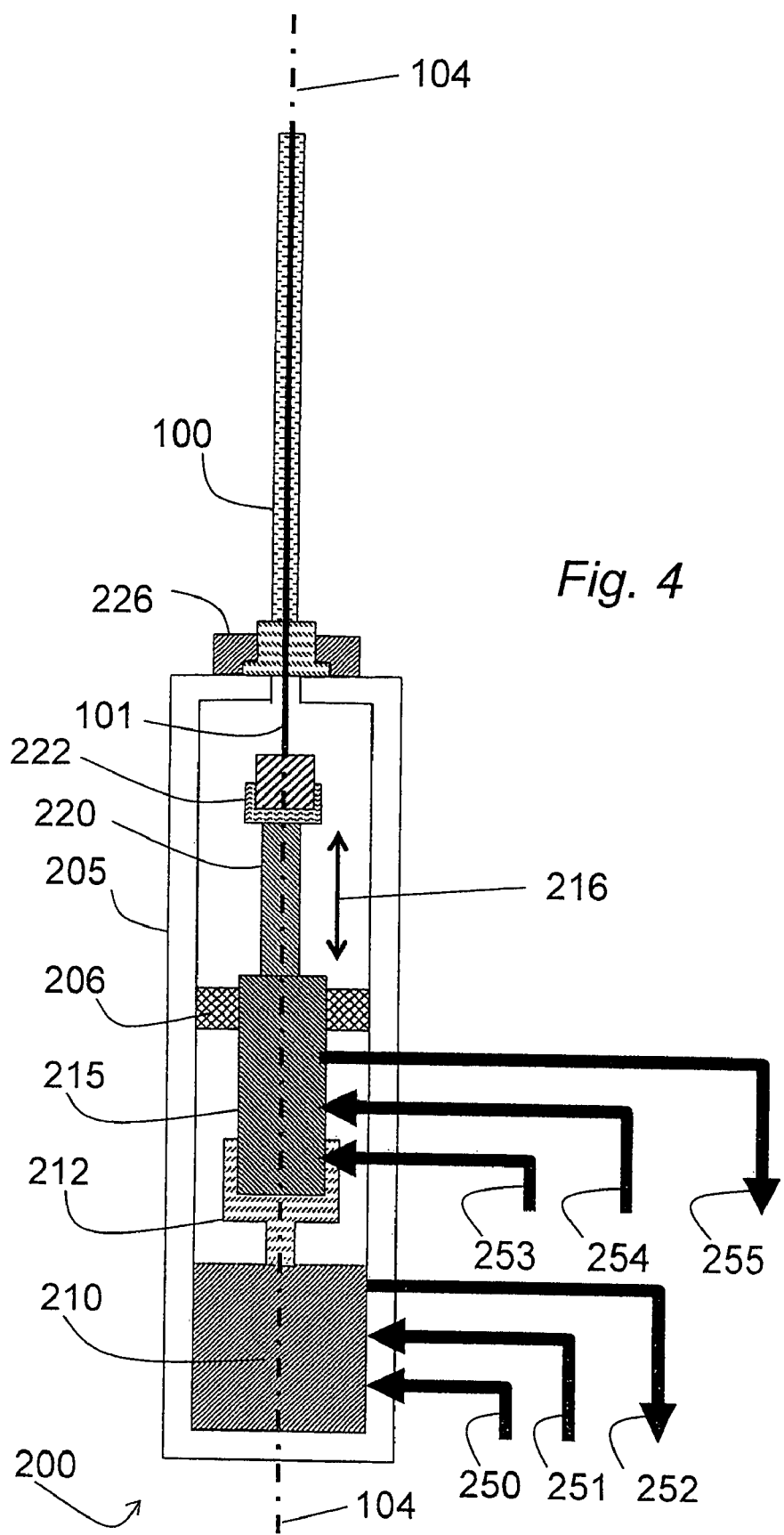
FIG. 4 is a sectioned view of the rotary and linear actuator combination in the needle actuation assembly.

It will be apparent that alternative designs to the one shown in FIG. 4 may be used—for example the position of the actuators may be changed so that actuator 210 is replaced by a linear actuator translating via a member 212 a rotary actuator replacing actuator 215. Rotary bearing 206 could be replaced by a linear bearing or guide.

Figure 5:
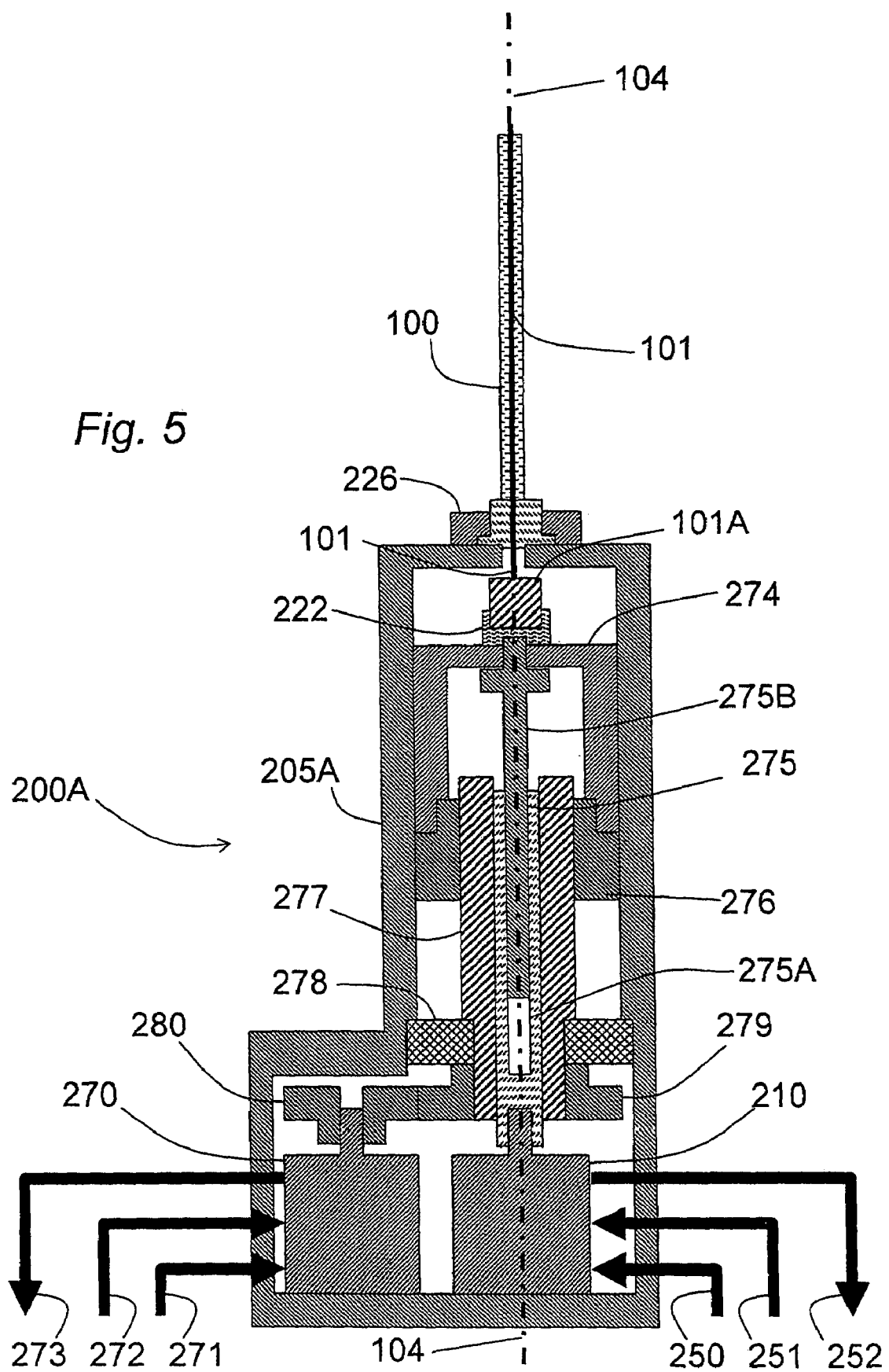
FIG. 5 is a sectioned view of an alternative needle actuation assembly with two rotary actuators.

An alternative embodiment for an actuated needle structure is shown in FIG. 5. In this embodiment, two rotary actuators are used instead of the combination of a rotary and linear actuator that was shown in FIG. 4. This embodiment has the advantage of simpler construction because rotary actuators are more readily available and less expensive than linear actuators. In this alternative actuator structure 200A, the axial motion of the stylet 101 with respect to the cannula 100 is achieved using a leadscrew 277 powered by rotary actuator 270. The rotation of the stylet 101 with respect to the cannula 100 is driven directly by rotary actuator 210 as in the previous embodiment that was shown in FIG. 4.

Rotary actuator 270, which drives the axial motion of the stylet 101, is mounted to the enclosure 205A and turns the driving gear 280. The driving gear 280 meshes with the driven gear 279 which is rigidly mounted to a hollow leadscrew 277 which rotates freely on an extendable (telescoping) shaft 275 extending therethrough and connected to the rotary actuator 210 to deliver the rotary motion thereof to the stylet 101 as will be described below. Rotation of the leadscrew 277, which is supported by bearing 278, causes the leadscrew nut 276 to translate along the axis of the leadscrew 277. The leadscrew nut 276 is rigidly mounted to a linear slider 274 which is free to slide within the enclosure 205 but is constrained against rotation about the axis 104 of the leadscrew 277.

A stylet locking mechanism 222 is positioned axially by the linear slider 274 but is free to rotate about the axis 104 of the leadscrew 277. The stylet 101 is rigidly mounted in the locking mechanism 222. The cannula 100 is rigidly attached to the enclosure 205 using the locking mechanism 226.

By controlling the rotation of the driving gear 280 with respect to rotary actuator 270, the extension of the stylet 101 with respect to the cannula 100 can be controlled. Rotary actuator 210 is rigidly mounted to the enclosure 205A and drives the rotation of the drive portion 275A of a telescoping shaft 275 which is coupled (keyed) to the driven portion 275B to permit relative axial motion while preventing relative rotational movement. The driven portion 275B is connected to the slider 274 and moves axially therewith while permitting rotary motion therebetween. The telescoping shaft 275 transmits rotary motion from rotary actuator 210 to the stylet locking mechanism 222 but the length of the telescoping shaft 275 is freely variable which allows the axial positioning of the stylet 101 to be independently controlled. By controlling the rotation of the telescoping shaft 275 with respect to the rotary actuator 210, the angle of the stylet 101 with respect to the cannula 100 can be controlled. The same power supply, actuation signal, and position sensing considerations from the previous embodiment (shown in FIG. 4) apply to the FIG. 5 embodiment. Power supplies 250 and 271 are schematically shown as inputs to the rotary actuators 210 and 270 respectively. Alternatively, the actuators can be supplied by power from batteries mounted internal to the needle actuator structure 200A. Actuation signals 251 and 272 are schematically shown as inputs to rotary actuators 210 and 270 respectively. Again, the actuators will contain typically a built-in sensor to measure the true displacement. The angular displacement signals 252 and 273 are schematically shown as outputs from rotary actuators 210 and 270 respectively. The angular displacement 273 can be converted easily to linear displacement of the stylet 101 by multiplication of the gear ratios among gears 279, 280 and lead screw nut 276.

Steering Control System

Figures 6A, 6B:
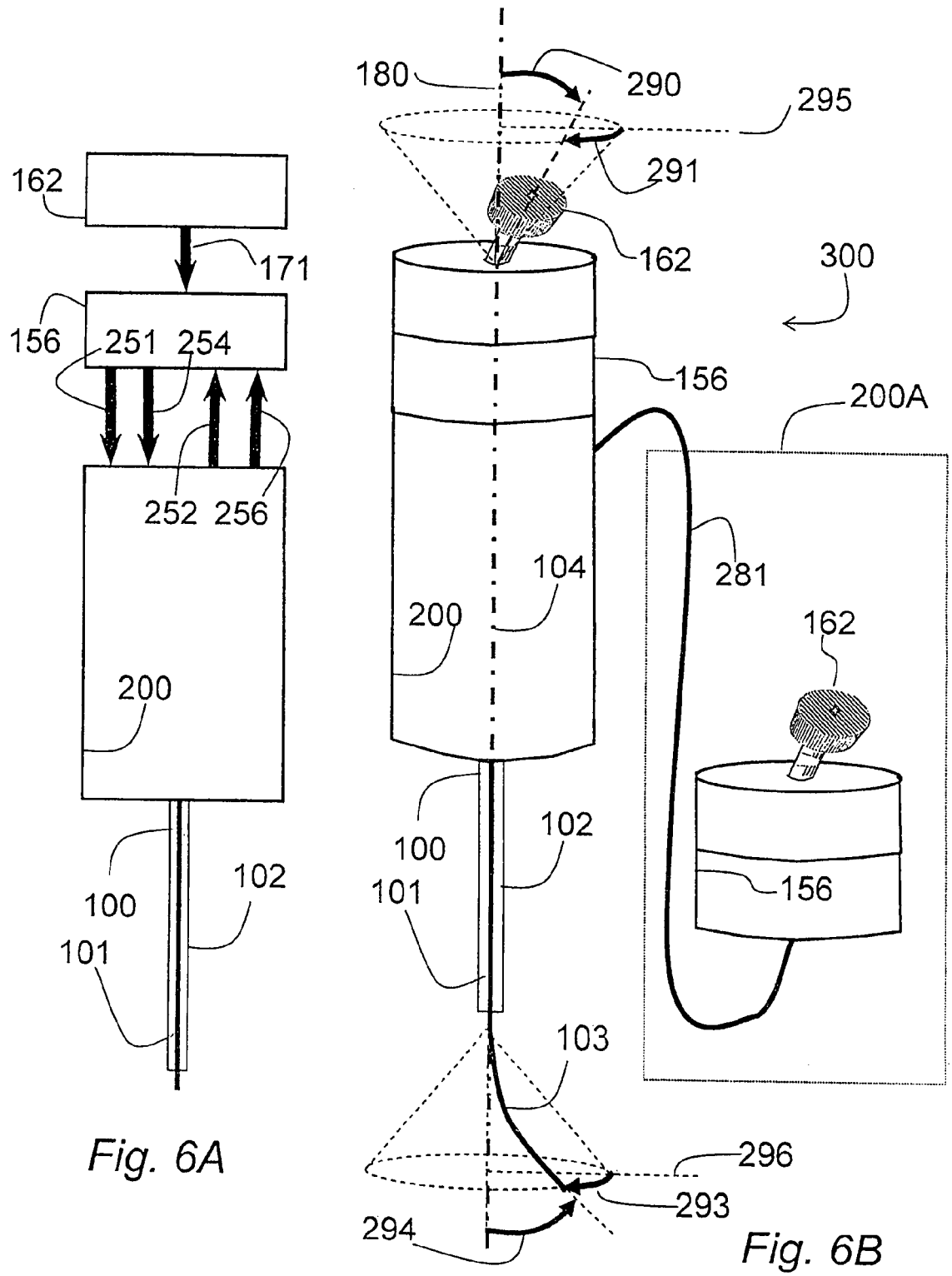
FIG. 6A shows the information flow between the joystick, the steering control system and the needle actuator structure.
FIG. 6B shows the actuation systems under joystick control, showing how joystick movements are converted into needle-tip steering.

The above embodiments clearly show that there are many ways in which the extension and angle of the stylet 101 with respect to the cannula 100 can be actuated. It is preferred that the operator steer the needle 102 with an intuitive interface instead of commanding the actuators directly. To this end the system as schematically illustrated in FIG. 6A is provided with an operator interface device 162 and a steering control unit 156 to steer the needle 102.

The interface device 162 is preferably a miniature joystick, although a set of pushbuttons, thumb-wheels or other similar devices could be used instead. The disclosure will describe the preferred version with a joystick. The manipulation of the joystick 162 produces a stream of steering commands 171 as inputs to the steering control unit 156. The steering control unit 156 then converts these steering commands 171 into desired actuator set-points that represent desired extension and rotation of the stylet 101. The steering control unit 156 also has input from the true angular displacement 252 and the true linear displacement 256 to provide feedback on the true extension and rotation of the stylet 101. The steering control unit 156 converts the inputs into the linear actuator control signal 251 and the rotary actuator control signal 254 using the well-established control strategy of proportional feedback control. In this strategy, the actuator control signals 251 and 254 are simply set to the difference between the desired steering commands 171 and the actual steering from feedback displacement signals 252 and 256, i.e. to the error between desired and actual signals.

Alternatively, more sophisticated known control strategies can be used such as proportional-derivative control, integral control or other similar strategies. As another alternative, less sophisticated known control strategies can be used such as open-loop control where the angular displacement sensor 252 and the linear displacement sensor 256 are not used.

For all control strategies, the actuator commands 251 and 254 are currents and voltages that are suitably converted to match the actuator requirements by appropriate interface electronics such as voltage to current converters, pulse-width modulation circuits, H-bridges and other known similar actuator interfaces.

The preferred implementation of steering control is shown in FIG. 6B. The joystick 162 is mounted on the needle actuator structure 200, preferably at the opposite end relative to the cannula 100 and stylet 101. The joystick 162 contains springs to center the joystick when released by the operator. Mounting of the joystick 162 at the end of the needle actuator structure 200 allows the operator to employ a power-grip to hold the assembly between the four fingers and the palm, while manipulating the joystick 162 with the thumb. Alternatively, the joystick 162 can be mounted on the side of the needle actuator structure 200 to allow the operator to employ a similar power grip but with the thumb near the cannula 100 and stylet 101. As another alternative, the joystick 162 can be placed adjacent to the needle actuator structure 200, such as on a desktop (see the insert in the box 200A in FIG. 6B). This allows the operator to hold the needle actuator structure 200 with one hand while manipulating the joystick 162 with the other hand. As a further alternative a second operator may be used to manipulate the joystick 162 while a first operator holds the needle actuator structure 200.

In all implementations, the steering control system 156 creates an interface between the joystick 162 and needle actuator structure 200. When the joystick 162 is located spaced from and generally adjacent to the needle actuator structure 200, an external cable 281 is used to connect the joystick 162 with the needle actuator structure 200. Alternatively, the external cable 281 can be replaced by a wireless communication system.

The movement of the joystick 162 normally will be mapped to needle-tip steering in an intuitive manner. As shown in FIG. 6B, the joystick 162 can be moved with two degrees of freedom—the deflection angle 290 of the joystick from its datum axis 180 (which in the embodiment of FIG. 6A is in axial alignment with the main axis 104 of the device 200), and the direction angle 291 measured around the axis 180 from a pre-defined lateral axis (or plane axial of the axis 180) 295 provide the inputs for axial and rotational movement respectfully of the stylet 101 relative to the cannula 100.

Normally the steering control unit 156 will make the angle 293 at which the curved end of the stylet 103 exits the cannula 100 equal to the joystick direction angle 291, angles 291 and 293 being measured with respect to the reference axes 195 and 196 respectively (196 being the initial or datum plane relative to the mail axis 104 of the needle 102 i.e. of the cannula 100. Normally the steering control unit will make the exit angle 294 of the curved tip of the stylet 103 with respect to the longitudinal axis 104 of the needle actuator structure 200 equal to the joystick deflection angle 290. Thus the deflection angle controls the axial extension of the stylet 101 with respect to the cannula 100 as required to achieve a deflection equivalent to the joystick deflection 290.

The control unit 156 converts the angles 290 and 291 into needle heading angles 293 and 294 and the conversion factors can be computed from simple planar geometry in the case in which the stylet is extended in free space (i.e. correlated with a preset curvature 103 for a given projection of the stylet 101 from the cannula 100. Generally greater stylet extensions correspond to greater values of the angle 294 and therefore greater magnitudes of steering. Alternatively, the deflection angle 290 of the joystick 162 may be mapped proportionally to the extension of the stylet 101, so that the needle heading angle 294 increases in a pre-selected relationship with the joystick deflection angle 290.

In summary, the entire needle steering device 200 works as follows: the direction of the joystick 162 determines the direction of the steering, and its deflection determines the extent of steering. Different kinematic mapping laws, not necessarily proportional, from the joystick deflection to the stylet heading angle 294 or stylet extension can be implemented, as conventionally done with computer input devices, the only basic requirement being that the stylet extension and angle 294 increase monotonically with joystick deflection.

The needle actuator structure 200, combined with the control units 156 and joystick 162, will be referred to as a needle steering device 300 (see FIG. 6). For a percutaneous procedure with the needle steering device 300, the operator picks a needle insertion point on the body that is on a desired needle path needed to reach a target 105 inside the body. The operator then provides both a force along the needle 102 to drive the needle into the body and steering inputs to the joystick 162 to maintain the needle 102 along the desired path.

An additional medical imaging system, such as ultrasound, fluoroscopy, computed tomography or magnetic resonance imaging, may be employed to allow the operator to see the current needle position with respect to the target.

The simplest application is a straight desired path. If the needle 102 starts to deviate from the desired straight line, the operator will manipulate the joystick 162 at an angle 291 in the direction from the current needle tip position to the desired path. The operator will also move the joystick 162 at an angle 290 in proportion to the amount of deviation from the desired path. The operator simultaneously drives the needle deeper into the body and manipulates the joystick 162 to steer the needle 102. If no correction is required, the joystick 162 is released, the stylet 101 is fully retracted into the cannula 100, and no tip steering is provided.

Another case is a desired path with a single planar curve. In this case, the operator pushes the joystick 162 at a direction angle 291 in the direction of the curve. Typically the operator continues to hold the joystick 162 at this angle while the needle 102 follows the curve. Deviations from the desired path are corrected by movements of the joystick direction angle 291 in the direction opposite to the deviation error, and an extension angle 290 proportional to the amount of deviation. More complicated paths can be created through combinations of the previous two cases. In all cases, the minimum radius of path curvature is determined by a number of factors including the length of cannula 100 and length of stylet 101, as well as stiffness of the cannula 100, stylet 101, and surrounding tissue.

Freehand Ultrasound Needle Guidance

The present invention can provide a medical imaging system that is used to help guide the operator. Ultrasound is typically used to monitor percutaneous needle insertions, and is the modality preferably used with needle tip steering. In this embodiment, a standard 2D ultrasound machine produces images through a hand-held probe 146 that is placed in contact with the body. The video display of the ultrasound machine shows a series of images created from ultrasound echoes in the plane determined by the probe. These cross-sectional images are produced very rapidly and they depict the location of the needle as it is inserted toward the target. Alternatively, a 3D ultrasound machine could be used. In this alternative embodiment, the 3D ultrasound machine works in a similar manner except that a set of cross-sectional images is acquired in a small neighborhood.

Figure 7:
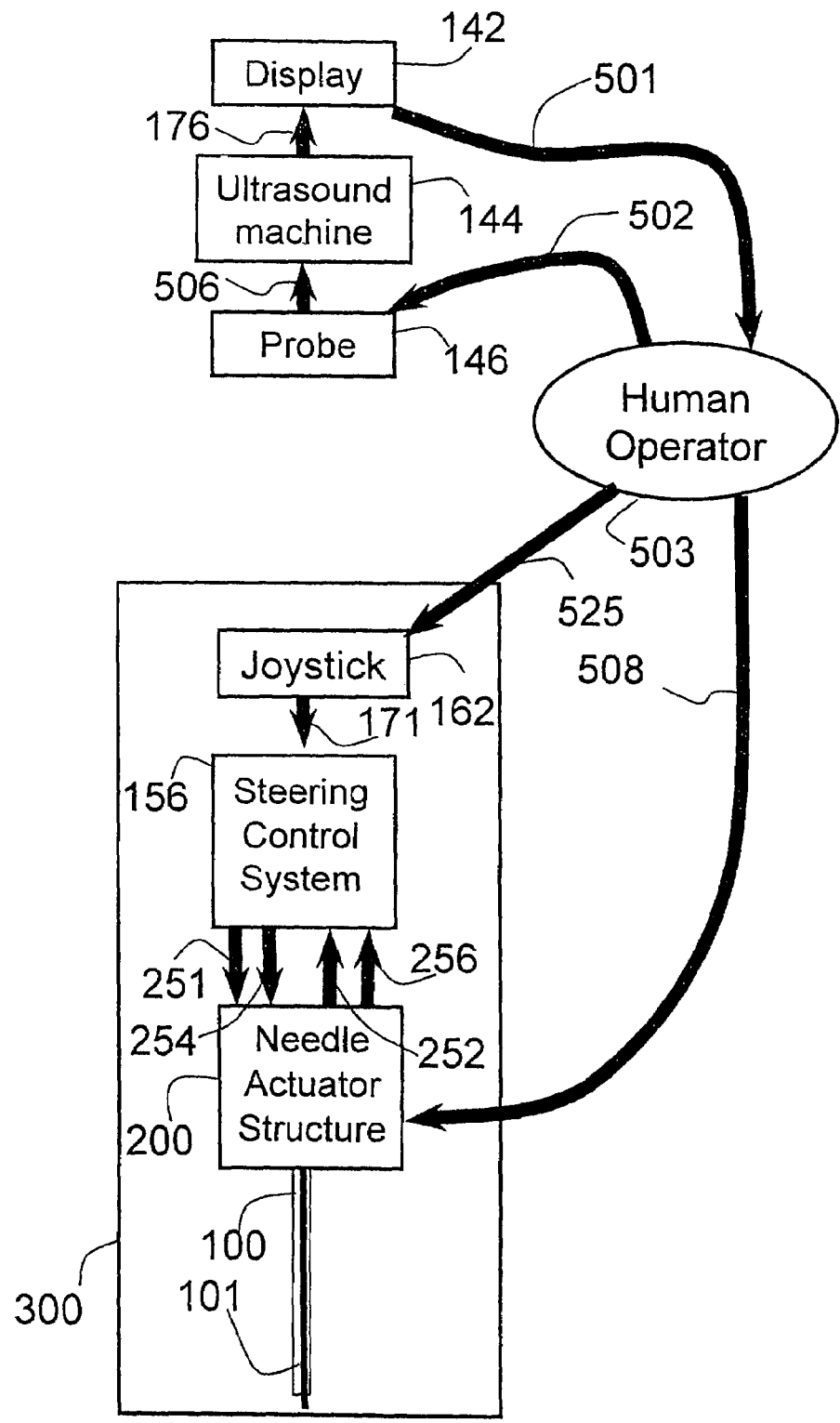
FIG. 7 shows how the operator conducts needle steering while simultaneously observing the needle insertion on a series of medical images.

With standard 2D ultrasound, the operator holds the ultrasound probe in one hand and the needle steering device 300 in the other hand. This is called freehand ultrasound needle guidance because both the probe and needle are free to move independently under the control of the operator's hand. The operator can determine the needle position from the images, observe a possible deviation from the desired path, and manipulate the joystick 162 to correct the deviation. The needle steering is done while the needle is being inserted. This operation is shown in FIG. 7.

The human operator 503 performs three actions: placement 502 of the ultrasound probe 146, joystick-control 525 i.e. manipulation of the joystick 162 and needle-driving 508 i.e. moving of the needle actuator structure 200 (cannula 100 and stylet 101). The operator 503 receives guidance 501 from the ultrasound display 142 showing the current needle position. The ultrasound probe 146 sends echoes 506 to the ultrasound machine 144 that, in turn, forms ultrasound images 176 and sends them to the display 142. The joystick steering commands 171 are converted to needle steering in the manner shown in FIGS. 6A and 6B.

The placement of the probe 146 to capture an image 176 of both the needle and the target is a difficult procedure that requires expertise by the operator 503. Clear images of the needle 102 are obtained only when the needle 102 falls precisely within the plane of the ultrasound probe 146. Furthermore, the ultrasound images 176 frequently contain noise and artifacts that obscure the needle 102. A needle detection system 332 (see FIG. 8A) is preferably used to determine where the needle 102 appears within a noisy ultrasound image, so it can be used for spatial localization of the needle, path planning, and as a visualization aid to help guide the operator, as shown later in FIG. 10.

Figure 8A:
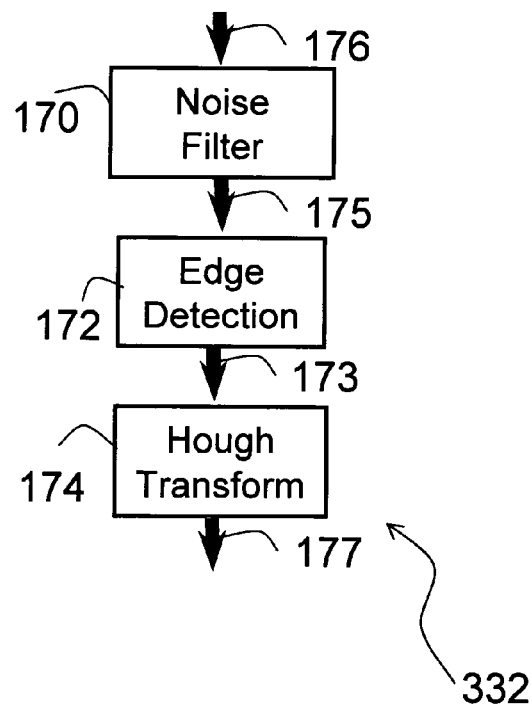
FIG. 8A shows the needle detection algorithm.
Figure 8B:
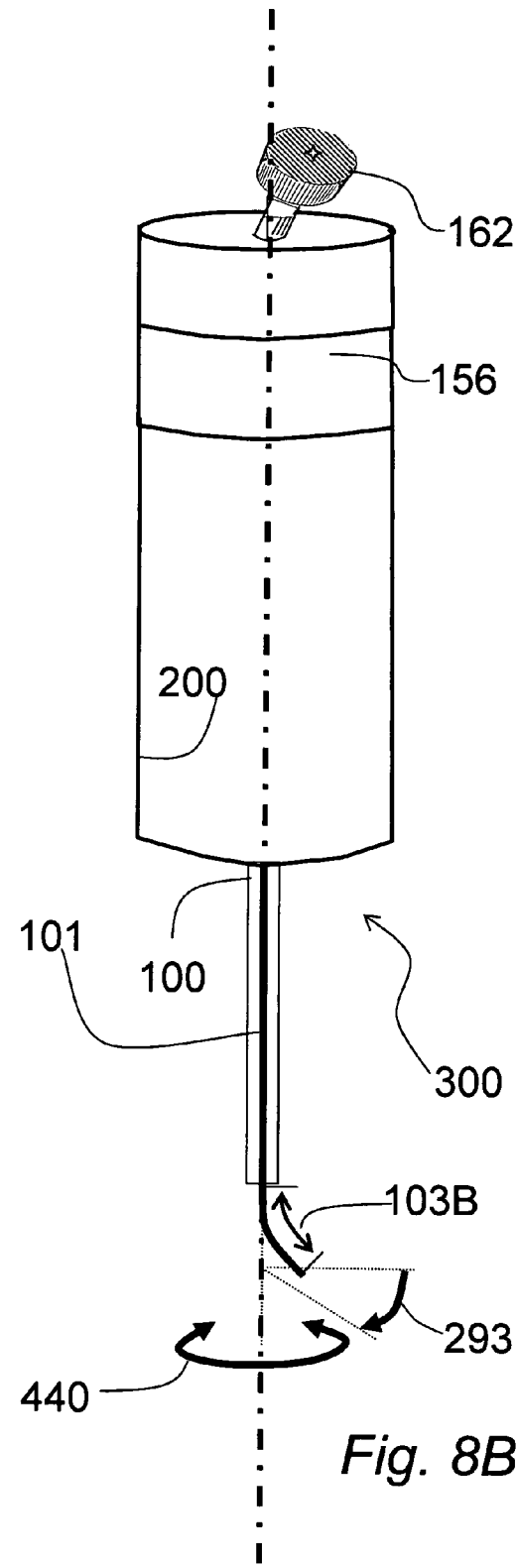
FIG. 8B shows the needle steering device while it is vibrating the needle tip to improve detection of the tip in a medical image.

An embodiment of the needle detection system is shown in FIG. 8A. The input to the needle detection system is the ultrasound image 176. The output is a polynomial 177 that parameterizes the curved appearance of the needle within the image. The needle detection system 332, consists of three stages, namely a noise filtering step 170, an edge detection step 172, and a Hough transform step 174. In a preferred embodiment, the noise filter step 170 uses a median filter to eliminate a significant amount of speckle noise. The output of the noise filter step 170 is therefore a smoothed image 175. The edge detection step 172 then calculates the derivative of the smoothed image 175, along a plurality of lines approximately perpendicular to a rough estimate of the needle position. A rough estimate of the needle position is determined beforehand by global search for the strongest edge in the image. Alternatively, an additional position sensor 148, described later in FIG. 10, can be used to estimate needle position. Two significant peaks are observed for each derivative function along each perpendicular line: one large positive peak denoting the edge of the first side of the needle 102, and one large negative peak denoting the edge of the second side of the needle 102. The average position between these two points is a guess at where the needle 102 crosses each perpendicular line, giving a plurality of points 173, most of which fall along the needle shaft. An initial linear fit is performed using these points 173 as a first approximation for the needle 102. A Hough transform 174 is used to increase the accuracy of the linear fit obtained form the edge detection step 172. The slope of the initial linear fit is rotated by N degree intervals up to +/−M degrees giving 2M/N rotated lines. The range of these slightly rotated lines is assumed to contain the actual slope of the needle axis. For each slope, the points 173 from the edge detection step 172 are projected onto the perpendicular of each rotated line. The line whose perpendicular projection produced the highest peak is chosen to represent the actual slope of the needle. The location of the highest peak on the perpendicular line defines a point through which the needle passes. The combination of this point and the slope defines the final linear equation of the needle. A threshold is then used to eliminate those points from the edge detection step that are too far from this line. Finally, a polynomial fit is applied to these remaining points to represent the curvature of the needle in mathematical form where the last detected point along the needle shaft is taken to be the tip. This polynomial curve 177 can be used as a visual aid to help guide the operator 503. Alternatively, the needle steering device 300 can be used in a novel way to help detect the tip of the needle 102 in an ultrasound image 176, as shown in FIG. 8B. The basic principle is to induce an oscillation in the tissue near the needle tip by commanding the rotation angle gamma 293 of the stylet 101 to apply a small motion pattern to said stylet for example to move the stylet in a small sinusoidal motion at a single frequency while extended from the cannula 100 (provide an actuator dedicated to applying a small motion pattern to the stylet 101 as described above for the FIGS. 14A, 14B and 14C embodiment). Most modern ultrasound machines are capable of measuring the spatial location of echoes that contain a Doppler shift. This capability is part of standard Doppler flow imaging, such as "Tissue Doppler Imaging" on the HDI5000 ultrasound machine (Philips Medical Solutions N.A., Bothell, Wash.). The oscillating tissue near the needle tip will produce Doppler shifts within a known range. If the frequency of oscillation is chosen slightly higher than oscillations normally found in the body, then the oscillating tissue near the needle tip can be easily detected. This improves the ability to detect the location of the needle tip within a noisy ultrasound image 176. Again, the detected needle tip can be used as a visual aid to help guide the operator 503.

FIG. 8B shows the stylet 101 with a short extended portion 103B slightly extended with respect to the cannula 100 and oscillating with a rotary motion about the axis 104 of cannula 100 (the angle 293 undergoes a sinusoidal motion). Alternatively, the stylet 101 extension 103B may be oscillated with respect to the cannula 100 to induce the Doppler shift. Alternatively, a combination of oscillations of stylet 101 rotation and extension with respect to the cannula 100 can be used to induce the Doppler shift.

Constrained Ultrasound Needle Guidance

Figure 9:
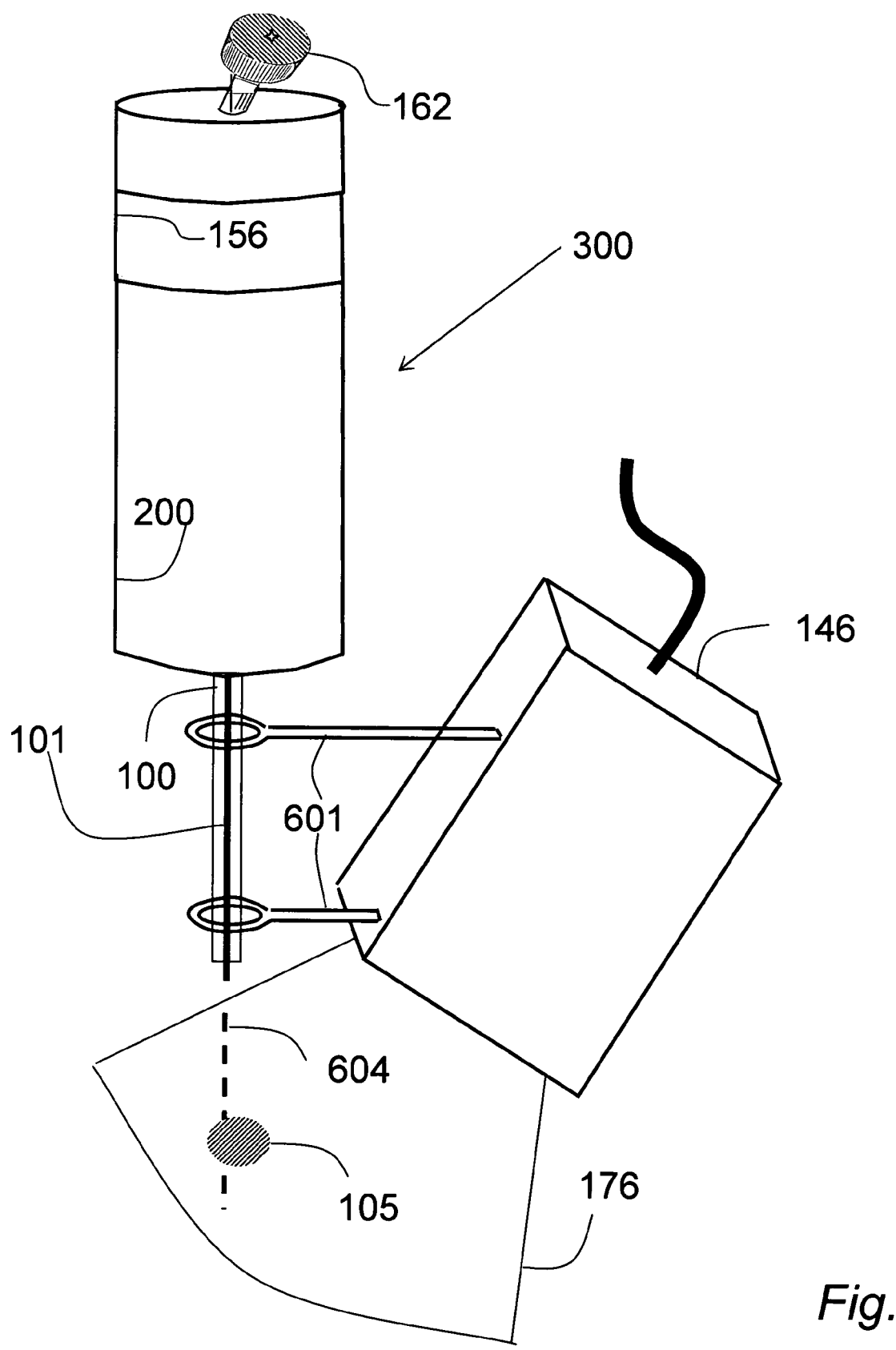
FIG. 9 shows an ultrasound probe and a mechanical constraint to assist the insertion of the needle, providing a known initial insertion path.

The previous section the freehand ultrasound needle guidance required the operator 503 to observe the needle 102 and target 105 on the ultrasound display 142 and then mentally calculate the correct steering to reach the target 105. This is a procedure that requires expertise in spatial orientation and hand-eye coordination for both conventional and steerable needles. With conventional needles, operators often utilize a mechanical needle guide attached to the ultrasound probe. A conventional mechanical guide 601 can also be used with the needle steering device 300, as shown in FIG. 9. The main goal is to constrain the insertion direction of the needle 102 to a fixed trajectory within the plane of the ultrasound probe 146. This gives the advantage of allowing the operator 503 to align the trajectory with the target 105 before the needle 102 is inserted. The disadvantage with conventional needles is that the needle often deflects away from the desired trajectory during insertion. The needle steering device 300 overcomes this disadvantage by allowing the operator 503 to steer the needle 102 to maintain the desired trajectory.

The procedure is performed as follows. The ultrasound probe 146 is placed at a location to clearly depict the target 105. The ultrasound machine 144 also superimposes a straight-line visual aid 604 on the ultrasound image 176 that shows the anticipated path of a perfectly rigid straight needle constrained by the mechanical needle guide 601. The location of the visual aid 604 is determined by the ultrasound machine 144 from knowledge of the mounting location of the guide 601 with respect to the probe 146 and thus with respect to the image 176. The operator 503 then adjusts the location of the ultrasound probe 146 until the straight line graphic 604 intersects the target 105. The needle steering device 300 is then inserted into the mechanical needle guide 601 and driven into the body. Any deflection of the needle 102 is seen as a deviation between the needle 102 and the straight line graphic 604 on the ultrasound image 176. The operator 503 then steers the needle 102 to return to the straight-line path that intersects the target 105. Deviations of the needle within the imaging plane 176 of the ultrasound machine can be seen and corrected by moving the joystick 162 in the direction opposite to the deviation, with an extension proportional to the deviation, as described before in the steering control section.

Deviations of the needle orthogonal to the imaging plane 176 of the ultrasound machine can be corrected in two ways—by recovering the needle tip image by rotating the ultrasound transducer 146 about the longitudinal axis of the needle steering device 300 (same as the undeflected cannula axis 100 in FIG. 9), and by steering the needle using the joystick in a direction perpendicular to the ultrasound imaging plane 176 in a trial-and-error search. The needle can be steered first on one side of the ultrasound plane by moving the joystick in that direction, and the needle can be pushed in a little. If the tip does not re-appear in the image, the opposite direction can be tried next. Finally, the oscillation technique presented in the previous section can be used with Doppler and slight motion of the ultrasound probe to determine on which side of the ultrasound plane is the needle tip located.

Computer Assisted Needle Guidance

In some cases, it is difficult to place the ultrasound probe 146 and needle guidance device 601 together so that both cross the target. For example, the presence of ribs limits the footprint that the probe 146 and guidance device 601 can occupy.

The following description describes an embodiment of a computer-assisted needle steering and guidance system.

In this embodiment, the freehand ultrasound needle guidance method described earlier is supplemented with a position sensor and a computer with specialized computer software 515. The position sensor 148 measures all six degrees of freedom (position and orientation) of both the ultrasound probe 146 and the needle steering device 300 with respect to a stationary coordinate system. One embodiment of this sensor 148 is an electromagnetic sensor, such as The BIRD (Ascension Technology Corporation, Burlington, Vt.) or FASTRAK (Polhemus Inc., Colchester, Vt.). Passive mechanical arms with joint angle sensors such as the FARO arm can be used to measure one or both positions of the ultrasound transducer 146 and needle steering device 300. These techniques have been documented in the kinematics sections of a number of robotics texts. Such mechanical arms can also be made lockable by using joint brakes. A number of papers such as the one identified above report the development lockable arms with joint sensors and pneumatic and electric brakes.

Figure 10:
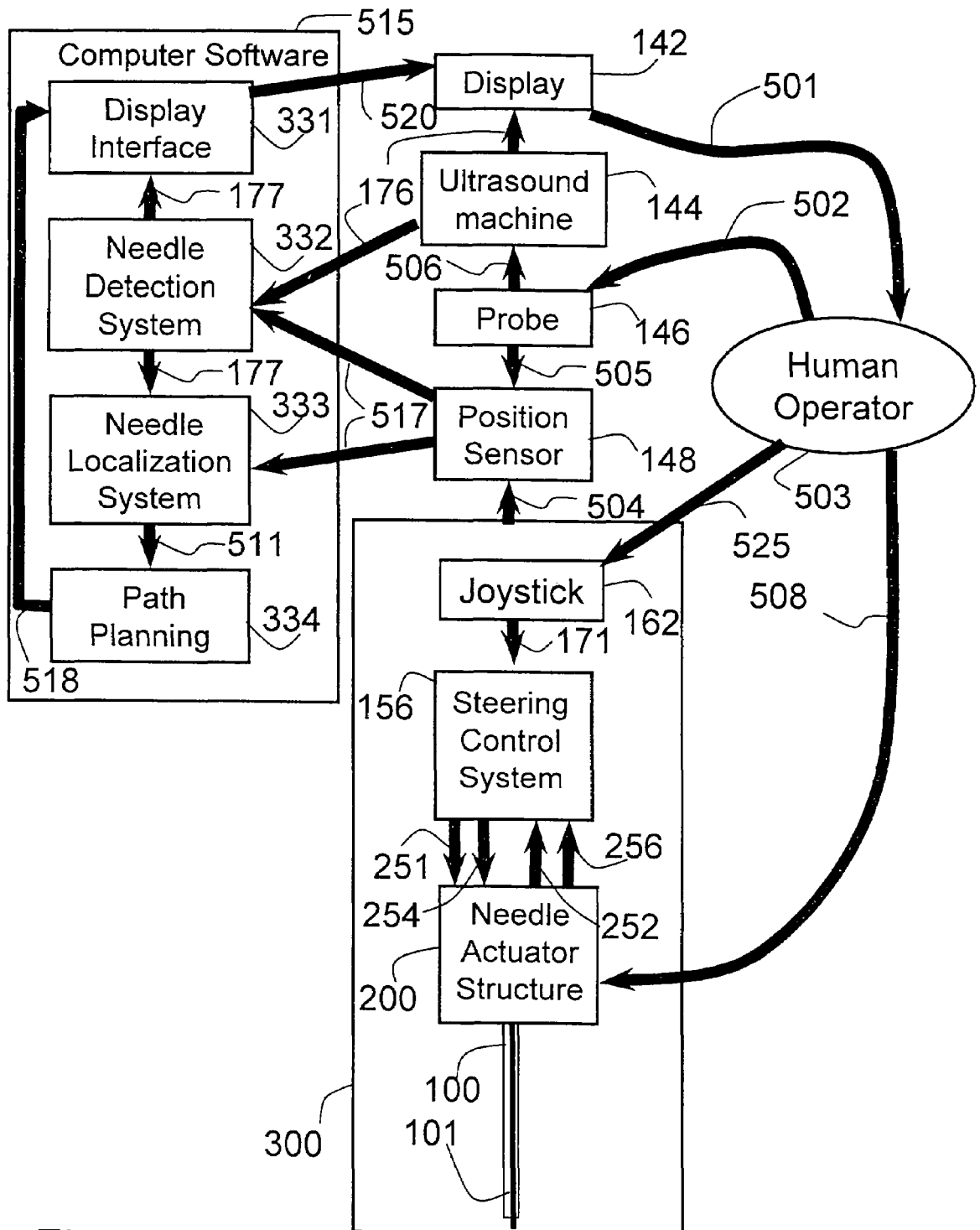
FIG. 10 shows computer assisted needle guidance, where the operator is provided with visual aids on current and desired paths.

As shown in FIG. 10, the operator 503 drives and steers as indicated schematically by arrows 508 and 525 respectively the needle based on guidance 501 provided by the ultrasound display 142, similar to the freehand ultrasound needle guidance shown in FIG. 7. But in this embodiment, the ultrasound display 142 provides additional information not available in freehand ultrasound needle guidance. As the ultrasound probe 146 and needle steering device 300 are moved by hand, the position sensor 148 sends the relative positions 517 to the needle detection system 332 and the needle localization system 333. The needle detection system 332, described earlier, uses the images 176 from the ultrasound machine 144 to determine the polynomial 177 describing where the needle 102 appears in the image 176. The needle detection system 332 uses the relative positions 517 of the probe 146 and the needle steering device 300 to establish an initial search region for the needle 102. This improves needle detection efficiency. The needle detection system 332 then passes the polynomial 177 to both the display interface 331 and the needle localization system 333.

The needle localization system 333 calculates the location of the needle 102 in the three dimensional space of the patient, unlike the polynomial 177 which describes the needle location with respect to the plane of the probe 146. The needle localization system 333 combines the polynomial, the positions 517 of the needle steering device 300 and the probe 146 to calculate the needle position in three-dimensional space. This is possible because the position sensor 148 measures both the positions of the probe 146 and the needle steering device 300 with respect to a fixed coordinate system. The fixed coordinate system is normally chosen as the coordinate system of the bed on which the patient lies. Thus, if the patient does not move with respect to the bed, then the needle position can be calculated with respect to the patient. This is called the patient-space needle position 511. In this embodiment, the patient-space needle position 511 is passed to the path planning system 334 which compares it to past needle positions to provide needle path information 518. The needle path information 518 is then sent to the display interface 331. The display interface 331 then superimposes the path information 518 on the ultrasound images 176 and sends the fused image 520 to the display 142. This embodiment provides the operator 503 with more complete guidance 501 about path planning in three-dimensional space to help steer the needle 102 to the target 105.

Preferably the medical imaging system and the computer software 515 operate in real-time, that is, the ultrasound display 142 is continuously updated during a procedure such that it always provides guidance with minimal delay.

As mentioned above, when ultrasound is used as the medical imaging system, then position sensors 148 are then attached to both the ultrasound probe 146 and needle steering device 300. For other medical imaging systems, such as magnetic resonance, computed tomography or fluoroscopy, the needle position is still measured and is measured with respect to the coordinate system of the medical imaging system. In this way, the needle localization system 333 can still calculate the needle position 511 in three-dimensional space.

Two alternative embodiments of the entire needle steering and guidance system will be described in the following two sections. In previous embodiments, the operator alone has performed the needle steering via the joystick. But allowing the computer to steer the needle provides more precise control and better accuracy in reaching a target. It also removes deleterious effects such as operator fatigue and operator ability from the procedure. These alternative embodiments improve the accuracy of the procedure, albeit with added complexity.

Computer Operated Needle Steering

Figure 11:
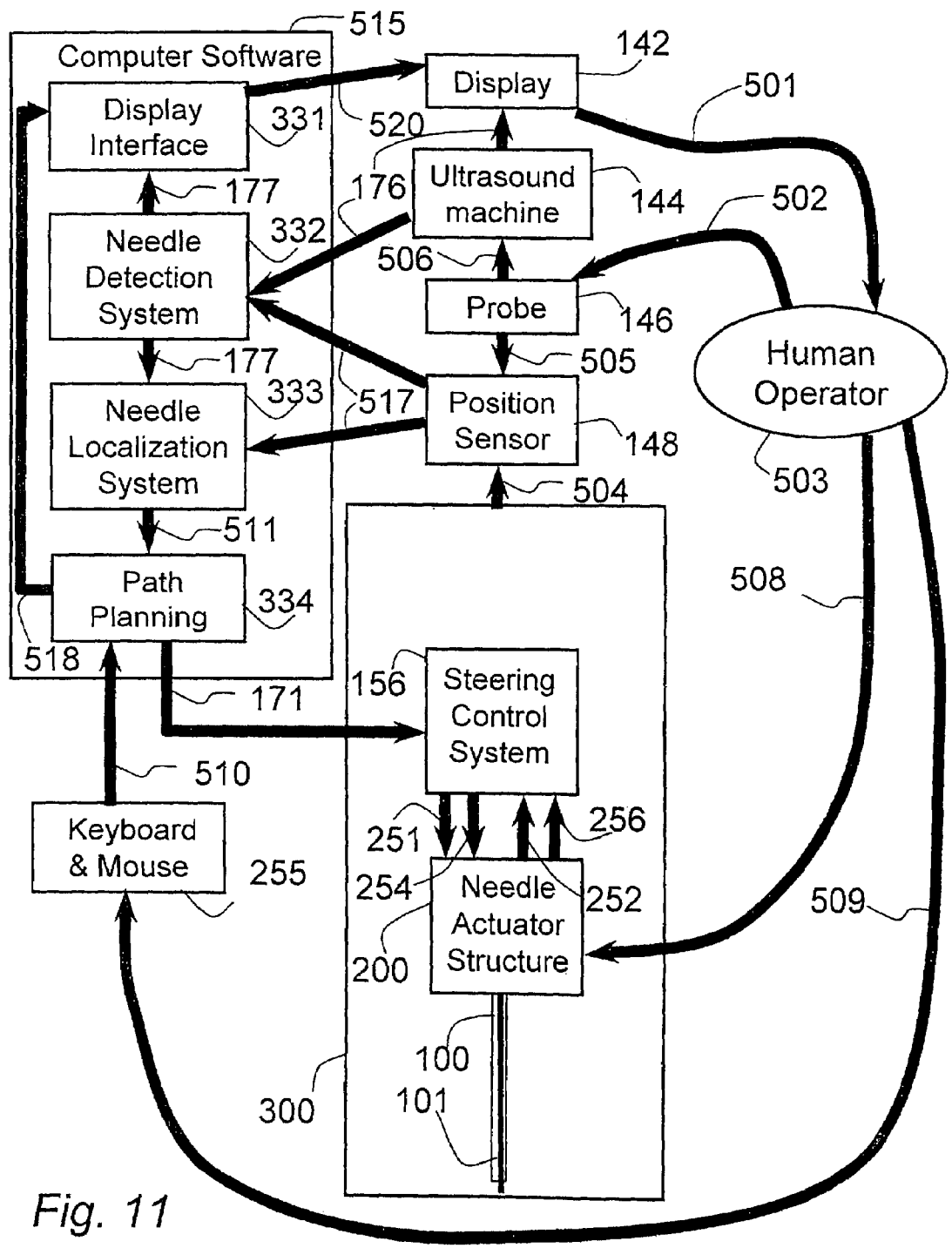
FIG. 11 shows computer operated needle steering, where the computer performs the steering, and operator supplies the driving force.

In this embodiment, the computer operated needle guidance is similar to the computer assisted needle guidance, shown in FIG. 10, but modified to allow the computer software 515 to control the needle steering instead of the operator 503. As shown in FIG. 11, the operator 503 still supplies the driving force 508 for the needle 102. The operator 503 also watches the ultrasound display 142, manipulates an ultrasound probe 146 to capture medical images 176 of the patient's body, and drives the needle actuator structure 200. Prior to the needle insertion, the operator 503 has a mental model of the target 509 and defines the desired path 510 using the operator input system 255, such as a keyboard and mouse. The path planning module now performs a more complicated task by not only providing the path 518 to the display interface 331, but also the steering commands 171 to the steering control system 156. This embodiment retains operator control over the driving of the needle 102 and thus retains the safety measures of freehand ultrasound needle guidance. But computer control of the steering improves the efficacy of the procedure.

Robot Operated Needle Driving and Steering

Figure 12:
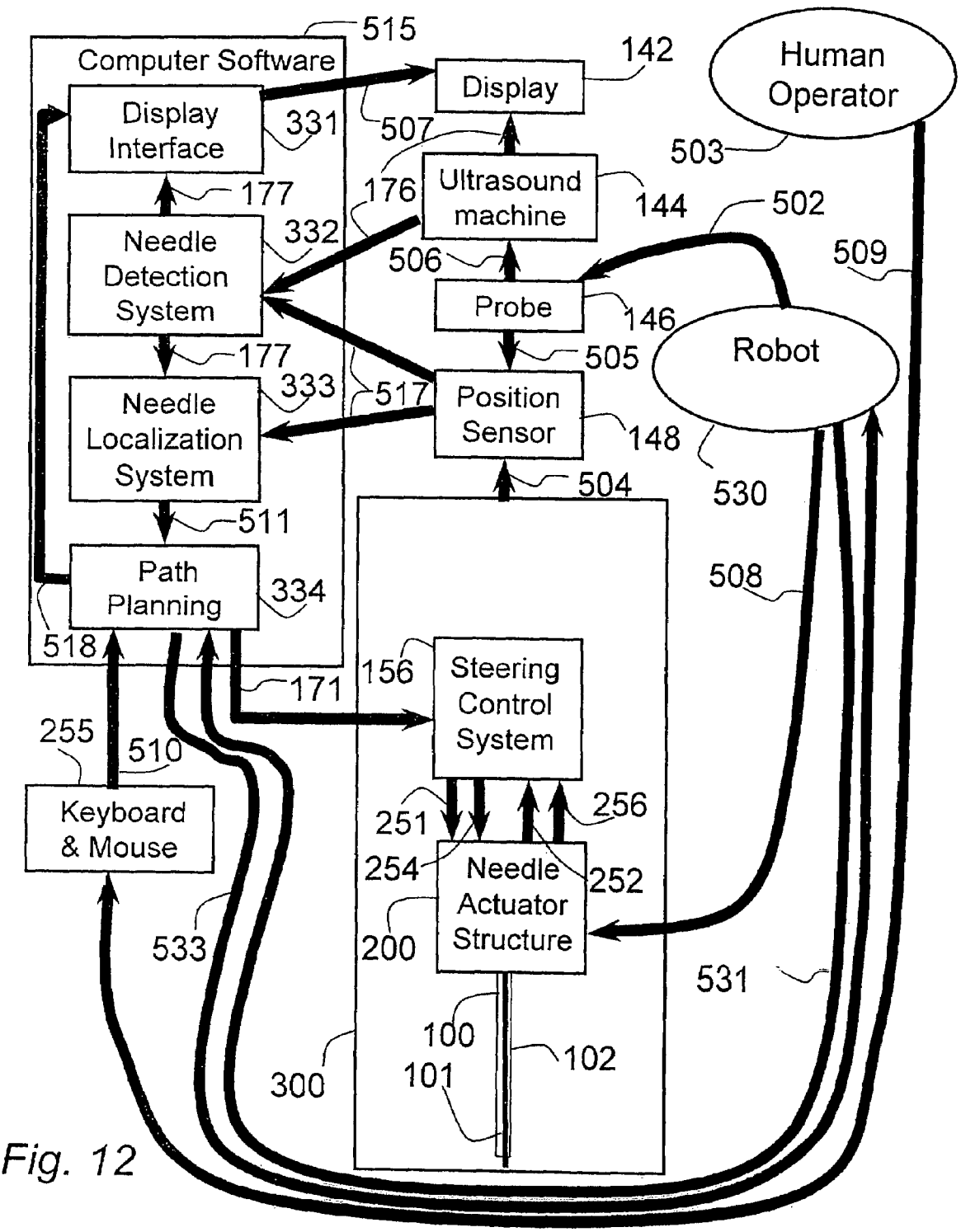
FIG. 12 shows robot operated needle driving and steering, where the computer controls both the steering and driving force.

A second alternative embodiment is to replace the human operator 503 with a robot 530, as shown in FIG. 12. The operation is similar to computer operated needle steering (FIG. 11), except that a robot 530 is used to drive the needle 102. This has the advantage of allowing the operator 503 to input simply the desired path 510 to the path planning module 334, and alleviates the need for the operator to drive the needle 102. This can be a significant advantage when fluoroscopic imaging or computed tomography imaging is used because it removes the operator 503 from exposure to ionizing radiation. It has the further advantage of allowing the robot 530 and needle steering system 300 to work in conjunction to drive the needle 102 more rapidly to the target 105.

The path planning module 334 is even more complicated in this embodiment because it is also requires the ability to command the robot motions 533. Unlike the human operator 503, the robot 530 can provide quantitative feedback 531 to the path planning module 334. This feedback 531, such as driving motion and driving force 508, can be used to continuously update the path planning throughout a needle insertion procedure. Additional safety measures must be added to the control of the robot 530. But computer control of both the needle driving and steering provides the highest level of accuracy in reaching the target.

Having described the invention modifications will be evident to those skilled in the art without departing from the spirit of the invention as defined in the appended claims.

We claim:

1. A steerable needle structure having a direction of advance toward a target that is changeable as said needle structure is being advanced toward said target comprising a hollow outer cannula having a main longitudinal axis and an open end located at the distal end of the outer cannula and a stylet, said stylet being longer than said cannula and having a leading end adjacent to said open end and having a curved portion with a pre-defined curvature adjacent to said leading end, mounting means mounting said stylet coaxially within said outer cannula so that said stylet and cannula may be relatively rotated and translated along said main axis from a sheathed position wherein substantially all of said curved portion of said stylet is within said cannula to and extended position wherein a selected extended part of said curved portion of said stylet distally projects beyond said open end, said cannula being stiffer than said stylet so that when said stylet is in its said sheathed position it assumes a shape primarily defined by said cannula, and when said stylet is in its said extended position, said extended part of said stylet assumes a curved shape primarily determined by said pre-defined curvature and length of said selected extended part, and said leading end extends from said cannula in a direction determined by the rotation of said stylet about said main axis and said curved shape so that when said needle structure is advanced with said stylet in said extended position said cannula is deflected toward said target and said direction of advance is changed as determined by said direction.

2. A needle structure as defined in claim 1 further comprising means for indicating said direction of said leading end.

3. A needle structure as defined in claim 2 wherein said means for indicating comprises marking on said stylet.

4. A needle structure as defined in claim 1 further comprising a casing, drive means, said drive means including means to rotate said stylet about said main axis and means to relatively translate said stylet and said cannula along said main axis from said sheathed position to said extended position, said means to rotate and said means to translate being mounted within said casing.

5. A needle structure as defined in claim 4 wherein said means to rotate and said means to relatively translate are connected to said stylet and said cannula is fixed to said casing.

6. A needle structure as defined in claim 4 further comprising sensing means for sensing the rotation of said stylet relative to said casing and further means for sensing said extended position of said stylet, operator input means for specifying a desired said direction and a desired said extended position, and computer means for controlling said means for actuating said means to rotate and said means to relatively move to achieve said desired direction and desired extended position.

7. A needle structure as defined in claim 6 wherein said operator input means is mounted on said casing.

8. A needle structure as defined in claim 6 wherein said operator input means includes a stylet rotation control and a translation control means for controlling said means to rotate and said means to relatively translate respectively, said rotation control means determining said direction relative to said easing, and said translation control means determining said extended part.

9. A needle structure as defined in claim 6 further comprising a medical imaging system to sense the position of a target to which said needle structure is directed, computer means to provide a detected position of said cannula within the images provided by said medical imaging system, and display means for displaying said target and said detected position of said cannula to an operator.

10. A needle structure as defined in claim 9 further comprising sensing means for sensing the position of said needle structure, computer means fin expressing said sensed position of said needle structure in the coordinates of said medical imaging system, and means for superimposing said sensed position of said needle structure in said coordinates of said medical imaging system onto said display means to display said sensed position of said needle structure with said target and said detected position of said cannula in a manner to assist an operator in steering said needle structure.

11. A needle structure as defined in claim 1 further comprising a medical imaging system to sense the position of a target to which said needle structure is directed, computer means to provide a detected position of said cannula within the images provided by said medical imaging system, and display means for displaying said target and said detected position of said cannula to an operator.

12. A needle structure as defined in claim 9 further comprising a mechanical guide, said mechanical guide facilitating alignment of said cannula to the said display means.

13. A needle structure as defined in claim 11 further comprising a mechanical guide, said mechanical guide facilitating alignment of said cannula to the said display means.

14. A needle structure as in claim 9 wherein said computer means generates a path to said target and displays it on said display means.

15. A needle structure as in claim 11 wherein said computer means generates a path to said target and displays it on said display means.

16. A needle structure as defined in claim 6 further comprising means for applying a small motion pattern to said stylet, said small motion pattern being detectable by medical imaging techniques.

17. A needle structure as defined in claim 9 wherein said computer generates a sequence of said desired directions and said desired extended positions of said stylet relative to said cannula to effect a cannula path to said target at the operator moves said needle structure.

18. A needle structure as defined in claim 14 further comprising a robot and wherein said computer includes means for controlling said robot to insert said needle structure on said path.

19. A needle structure as in claim 1 wherein said cannula has a reinforced segment of higher stiffness adjacent to said open end.

20. A method of controlling the path of movement of a needle structure toward a target wherein said needle structure comprises a hollow outer cannula having a main longitudinal axis and an open end, a stylet having a curved portion having a pre-defined curvature adjacent to its leading end, said stylet being mounted coaxially within said outer cannula with said leading end adjacent to said open end, so that said stylet may be rotated about said main axis and said stylet and cannula relatively moved axially relative to said main axis between a sheathed position wherein said curved portion of said stylet is within said cannula to an extended position wherein said stylet projects a selected distance beyond said free end to provide a curved extended part of said stylet having a curvature approaching said pre-defined curvature with said leading end extending from said cannula in a controlled direction determined by rotation of said stylet about said main axis, said method comprising, moving said stylet and said cannula on said path in a selected direction toward said target and adjusting said selected direction by rotating said stylet within said cannula to a selected orientation and then relatively moving said stylet end said cannula to position said stylet in a selected said extended position, and to provide said curved extended part with said leading end pointing in said controlled direction determined by said selected rotation, said pre-defined curvature and said selected distance said stylet extends beyond said free end in said extended position then advancing said stylet and said cannula together as a unit with said stylet in said extended position along said path in an adjusted direction.

21. A method as defined in claim 20 where said relatively moving comprises moving said stylet relative to said cannula.

22. A method as defined in claim 20 further comprising detecting said needle in an ultrasound image by median filtering to remove speckle noise, detecting needle point candidates at the peaks in the derivative function along several directions perpendicular to an approximate direction of the needle, fitting such point candidates to a line, using a Rough transform to improve on the resulting line, and finding a polynomial fit to those needle point candidates that are close to the line determined by the Rough transform.

* * * * *